(12) United States Patent
Harris et al.

(10) Patent No.: US 12,714,423 B2
(45) Date of Patent: Aug. 25, 2026

(54) SURGICAL INSTRUMENTS WITH PROGRESSIVE JAW CLOSURE ARRANGEMENTS

(71) Applicant: Cilag GmbH International, Zug (CH)

(72) Inventors: Jason L. Harris, Lebanon, OH (US); Frederick E. Shelton, IV, Hillsboro, OH (US); Gregory J. Bakos, Mason, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/029,353

(22) Filed: Jan. 17, 2025

(65) Prior Publication Data

US 2025/0235210 A1 Jul. 24, 2025

Related U.S. Application Data

(63) Continuation of application No. 17/534,636, filed on Nov. 24, 2021, now Pat. No. 12,262,888, which is a continuation of application No. 16/105,094, filed on Aug. 20, 2018, now abandoned.

(51) Int. Cl.
*A61B 17/072* (2006.01)

(52) U.S. Cl.
CPC ...... *A61B 17/072* (2013.01); *A61B 17/07207* (2013.01); *A61B 2017/07228* (2013.01); *A61B 2017/07257* (2013.01); *A61B 2017/07271* (2013.01); *A61B 2017/07285* (2013.01)

(58) Field of Classification Search
CPC ................ A61B 17/068; A61B 17/072; A61B 17/07207; A61B 2017/2927; A61B 2017/2929
See application file for complete search history.

(56) References Cited

U.S. PATENT DOCUMENTS

| | | | |
|---|---|---|---|
| 4,834,096 | A | 5/1989 | Oh et al. |
| 5,338,317 | A | 8/1994 | Hasson et al. |
| 5,620,415 | A | 4/1997 | Lucey et al. |
| 5,662,667 | A | 9/1997 | Knodel |
| 5,697,542 | A | 12/1997 | Knodel et al. |

(Continued)

FOREIGN PATENT DOCUMENTS

| | | | |
|---|---|---|---|
| JP | 2013042921 | A | 3/2013 |
| WO | WO-2009046490 | A1 | 4/2009 |
| WO | WO-2016100682 | A1 | 6/2016 |

*Primary Examiner* — Joshua G Kotis

(74) *Attorney, Agent, or Firm* — Lempia Summerfield Katz LLC

(57) ABSTRACT

A surgical instrument that includes a first jaw and a second jaw that are movable between a closed position and an open position. An axially movable closure member is supported relative to the jaws to apply closing and opening motions thereto. A closure actuator operably interfaces with the closure member and is movable from an unactuated position corresponding to the open position in a closure direction during a closure procedure. A first control system is configured to apply an opening control motion to the closure actuator to return the closure actuator to the unactuated position upon completion of the closure procedure. A second control system is configured to apply a variable closure force to the closure member as the closure actuator is moved in the closure direction.

18 Claims, 21 Drawing Sheets

(56) References Cited

U.S. PATENT DOCUMENTS 5,833,696 A 11/1998 Whitfield et al.
5,842,993 A * 12/1998 Eichelberger ........ A61B 1/0051 600/462
6,458,142 B1 10/2002 Faller et al.
6,958,070 B2 10/2005 Witt et al.
7,582,086 B2 9/2009 Privitera et al.
7,597,693 B2 10/2009 Garrison
7,766,910 B2 8/2010 Hixson et al.
7,819,299 B2 10/2010 Shelton, IV et al.
7,918,848 B2 4/2011 Lau et al.
8,196,795 B2 6/2012 Moore et al.
8,317,070 B2 11/2012 Hueil et al.
8,393,514 B2 3/2013 Shelton, IV et al.
8,720,766 B2 5/2014 Hess et al.
8,893,949 B2 11/2014 Shelton, IV et al.
8,931,682 B2 1/2015 Timm et al.
9,681,870 B2 6/2017 Baxter, III et al.
9,700,319 B2 7/2017 Motooka et al.
9,801,679 B2 10/2017 Trees et al.
9,839,428 B2 12/2017 Baxter, III et al.
9,888,919 B2 2/2018 Leimbach et al.
10,172,616 B2 1/2019 Murray et al.
10,349,963 B2 7/2019 Fiksen et al.
10,471,282 B2 11/2019 Kirk et al.
10,537,381 B2 1/2020 Joseph et al.
10,568,652 B2 2/2020 Hess et al.
10,610,236 B2 4/2020 Baril
10,653,477 B2 5/2020 Nagtegaal
10,743,930 B2 8/2020 Nagtegaal
10,980,536 B2 4/2021 Weaner et al.
11,812,958 B2 * 11/2023 Morgan ............... A61B 17/072
2004/0094597 A1 5/2004 Whitman et al.
2006/0079874 A1 4/2006 Faller et al.
2008/0223903 A1 * 9/2008 Marczyk ............. A61B 17/135 227/175.1
2008/0255413 A1 * 10/2008 Zemlok ............. A61B 17/1155 600/106
2009/0090763 A1 * 4/2009 Zemlok ........... A61B 17/07207 227/175.2
2009/0270853 A1 10/2009 Yachi et al.
2010/0193568 A1 * 8/2010 Scheib ............ A61B 17/07207 227/176.1
2010/0211053 A1 * 8/2010 Ross ............... A61B 17/07207 606/1
2011/0017801 A1 * 1/2011 Zemlok ........... A61B 17/07207 227/175.1
2012/0022583 A1 1/2012 Sugalski et al.
2014/0249557 A1 * 9/2014 Koch, Jr. ............... A61B 90/98 606/170
2015/0133921 A1 5/2015 Strobl et al.
2015/0173746 A1 * 6/2015 Baxter, III ....... A61B 17/07207 227/176.1
2015/0173756 A1 6/2015 Baxter, III et al.
2015/0272575 A1 * 10/2015 Leimbach ............. A61B 90/96 227/175.3
2015/0297225 A1 10/2015 Huitema et al.
2016/0051316 A1 2/2016 Boudreaux
2016/0174976 A1 * 6/2016 Morgan ............... A61B 17/072 227/175.1
2017/0086930 A1 3/2017 Thompson et al.
2017/0340325 A1 11/2017 Baril et al.
2018/0168575 A1 6/2018 Simms et al.
2018/0289371 A1 10/2018 Wang et al.
2019/0142506 A1 5/2019 Miyajima et al.
2019/0201025 A1 * 7/2019 Shelton, IV ......... A61B 17/072
2019/0298353 A1 * 10/2019 Shelton, IV ..... A61B 17/07207
2020/0121377 A1 4/2020 Kitamura

* cited by examiner

60°
50°
2170A
2176
2172
2174
SA
EA
-60°
RA
1500
Stop
1000

SA
EA
$LA_2$
-10°
1500
Change Speed
1000

2170A
2176
2172
2174
EA
SA
$LA_1$
+10°
1500
Change Speed
1000

2170A
2176
2172
2174
SA
+60°
EA
LA
1500
Stop
1000

2170A
2176
2172
2174
-60°
Boundary
0°
Center
Home
+60°
Boundary

Traveler Geometry
A
B
C
2170A
2170B
2170C
2171C
$CT_A$
$CT_B$ $MS_{2A}$
$MS_{2B}$
$MS_{2C}$
$MS_{1A}$
$MS_{1B}$
$MS_{3B}$
-60
-30
0
+30
+60
ARTICULATION ANGLE
MOTOR SPEED

SURGICAL INSTRUMENTS WITH PROGRESSIVE JAW CLOSURE ARRANGEMENTS

CROSS-REFERENCE TO RELATED APPLICATION

This application is a continuation application claiming priority under 35 U.S.C. § 120 to U.S. patent application Ser. No. 17/534,636, entitled SURGICAL INSTRUMENTS WITH PROGRESSIVE JAW CLOSURE ARRANGEMENTS, filed Nov. 24, 2021, now U.S. Patent Application Publication No. 2022/0160355, which is a continuation application claiming priority under 35 U.S.C. § 120 to U.S. patent application Ser. No. 16/105,094, entitled SURGICAL INSTRUMENTS WITH PROGRESSIVE JAW CLOSURE ARRANGEMENTS, filed Aug. 20, 2018, now U.S. Patent Application Publication No. 2020/0054321, the entire disclosures of which are hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
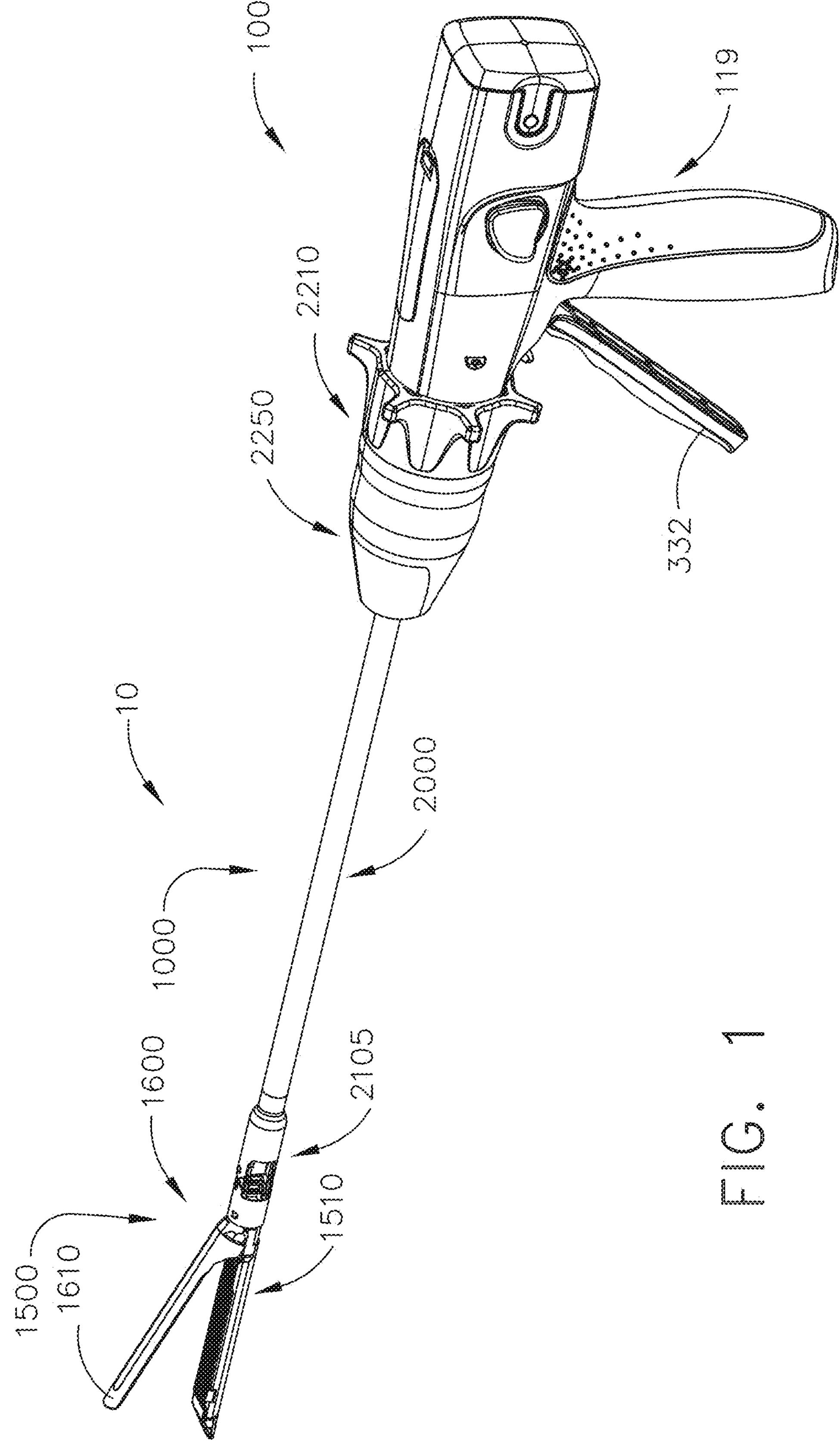
FIG. 1 is a perspective view of a powered surgical stapling system.

Applicant of the present application owns the following U.S. Patent Applications that were filed on Aug. 20, 2018 and which are each herein incorporated by reference in their respective entireties:

- U.S. patent application Ser. No. 16/105,101, entitled METHOD FOR FABRICATING SURGICAL STAPLER ANVILS, now U.S. Patent Application Publication No. 2020/0054323;
- U.S. patent application Ser. No. 16/105,183, entitled REINFORCED DEFORMABLE ANVIL TIP FOR SURGICAL STAPLER ANVIL, now U.S. Pat. No. 10,912,559;
- U.S. patent application Ser. No. 16/105,150, entitled SURGICAL STAPLER ANVILS WITH STAPLE DIRECTING PROTRUSIONS AND TISSUE STABILITY FEATURES, now U.S. Pat. No. 11,039,834;
- U.S. patent application Ser. No. 16/105,098, entitled FABRICATING TECHNIQUES FOR SURGICAL STAPLER ANVILS, now U.S. Pat. No. 11,045,192;
- U.S. patent application Ser. No. 16/105,122, entitled SURGICAL STAPLING DEVICES WITH IMPROVED CLOSURE MEMBERS, now U.S. Patent Application Publication No. 2020/0054324;
- U.S. patent application Ser. No. 16/105,140, entitled SURGICAL STAPLER ANVILS WITH TISSUE STOP FEATURES CONFIGURED TO AVOID TISSUE PINCH, now U.S. Pat. No. 10,779,821;
- U.S. patent application Ser. No. 16/105,081, entitled METHOD FOR OPERATING A POWERED ARTICULATABLE SURGICAL INSTRUMENT, now U.S. Patent Application Publication No. 2020/0054320;
- U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS, now U.S. Pat. No. 11,083,458;
- U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM, now U.S. Pat. No. 10,842,492;
- U.S. patent application Ser. No. 16/105,119, entitled ARTICULATABLE MOTOR POWERED SURGICAL INSTRUMENTS WITH DEDICATED ARTICULATION MOTOR ARRANGEMENTS, now U.S. Patent Application Publication No. 2020/0054330;
- U.S. patent application Ser. No. 16/105,160, entitled SWITCHING ARRANGEMENTS FOR MOTOR POWERED ARTICULATABLE SURGICAL INSTRUMENTS, now U.S. Pat. No. 10,856,870; and
- U.S. Design patent application Ser. No. 29/660,252, entitled SURGICAL INSTRUMENT ANVIL, now U.S. Design Pat. No. D914,878.

Applicant of the present application owns the following U.S. Patent Applications and U.S. Patents that are each herein incorporated by reference in their respective entireties:

- U.S. patent application Ser. No. 15/386,185, entitled SURGICAL STAPLING INSTRUMENTS AND REPLACEABLE TOOL ASSEMBLIES THEREOF, U.S. Patent Application Publication No. 2018/0168642;
- U.S. patent application Ser. No. 15/386,230, entitled ARTICULATABLE SURGICAL STAPLING INSTRUMENTS, U.S. Patent Application Publication No. 2018/0168649;
- U.S. patent application Ser. No. 15/386,221, entitled LOCKOUT ARRANGEMENTS FOR SURGICAL END EFFECTORS, U.S. Pat. No. 10,835,247;
- U.S. patent application Ser. No. 15/386,209, entitled SURGICAL END EFFECTORS AND FIRING MEMBERS THEREOF, U.S. Patent Application Publication No. 2018/0168645;
- U.S. patent application Ser. No. 15/386,198, entitled LOCKOUT ARRANGEMENTS FOR SURGICAL END EFFECTORS AND REPLACEABLE TOOL ASSEMBLIES, U.S. Patent Application Publication No. 2018/0168644;
- U.S. patent application Ser. No. 15/386,240, entitled SURGICAL END EFFECTORS AND ADAPTABLE FIRING MEMBERS THEREFOR, U.S. Patent Application Publication No. 2018/0168651;
- U.S. patent application Ser. No. 15/385,939, entitled STAPLE CARTRIDGES AND ARRANGEMENTS OF STAPLES AND STAPLE CAVITIES THEREIN, U.S. Patent Application Publication No. 2018/0168629;
- U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, U.S. Patent Application Publication No. 2018/0168630;
- U.S. patent application Ser. No. 15/385,943, entitled SURGICAL STAPLING INSTRUMENTS AND STAPLE-FORMING ANVILS, U.S. Patent Application Publication No. 2018/0168631;
- U.S. patent application Ser. No. 15/385,950, entitled SURGICAL TOOL ASSEMBLIES WITH CLOSURE STROKE REDUCTION FEATURES, U.S. Patent Application Publication No. 2018/0168635;
- U.S. patent application Ser. No. 15/385,945, entitled STAPLE CARTRIDGES AND ARRANGEMENTS OF STAPLES AND STAPLE CAVITIES THEREIN; U.S. Patent Application Publication No. 2018/0168632;
- U.S. patent application Ser. No. 15/385,946, entitled SURGICAL STAPLING INSTRUMENTS AND STAPLE-FORMING ANVILS, U.S. Patent Application Publication No. 2018/0168633;
- U.S. patent application Ser. No. 15/385,951, entitled SURGICAL INSTRUMENTS WITH JAW OPENING FEATURES FOR INCREASING A JAW OPENING DISTANCE, U.S. Patent Application Publication No. 2018/0168636;
- U.S. patent application Ser. No. 15/385,953, entitled METHODS OF STAPLING TISSUE, U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, U.S. Patent Application Publication No. 2018/0168639;

U.S. patent application Ser. No. 15/385,948, entitled SURGICAL STAPLING INSTRUMENTS AND STAPLE-FORMING ANVILS, U.S. Patent Application Publication No. 2018/0168584;

U.S. patent application Ser. No. 15/385,956, entitled SURGICAL INSTRUMENTS WITH POSITIVE JAW OPENING FEATURES, U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, U.S. Patent Application Publication No. 2018/0168634;

U.S. patent application Ser. No. 15/385,896, entitled METHOD FOR RESETTING A FUSE OF A SURGICAL INSTRUMENT SHAFT, U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, U.S. Patent Application Publication No. 2018/0168599;

U.S. patent application Ser. No. 15/385,899, entitled SURGICAL INSTRUMENT COMPRISING IMPROVED JAW CONTROL, U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, U.S. Patent Application Publication No. 2018/0168602;

U.S. patent application Ser. No. 15/385,902, entitled SURGICAL INSTRUMENT COMPRISING A CUTTING MEMBER, U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, U.S. Patent Application Publication No. 2018/0168605;

U.S. patent application Ser. No. 15/385,905, entitled FIRING ASSEMBLY COMPRISING A LOCKOUT, U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, U.S. Patent Application Publication No. 2018/0168608;

U.S. patent application Ser. No. 15/385,908, entitled FIRING ASSEMBLY COMPRISING A FUSE, U.S. Patent Application Publication No. 2018/0168609;

U.S. patent application Ser. No. 15/385,909, entitled FIRING ASSEMBLY COMPRISING A MULTIPLE FAILED-STATE FUSE, U.S. Patent Application Publication No. 2018/0168610;

U.S. patent application Ser. No. 15/385,920, entitled STAPLE-FORMING POCKET ARRANGEMENTS, U.S. Patent Application Publication No. 2018/0168620;

U.S. patent application Ser. No. 15/385,913, entitled ANVIL ARRANGEMENTS FOR SURGICAL STAPLERS, U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, U.S. Patent Application Publication No. 2018/0168615;

U.S. patent application Ser. No. 15/385,893, entitled BILATERALLY ASYMMETRIC STAPLE-FORMING POCKET PAIRS, U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, U.S. Patent Application Publication No. 2018/0168612;

U.S. patent application Ser. No. 15/385,927, entitled SURGICAL STAPLING INSTRUMENTS WITH SMART STAPLE CARTRIDGES, U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, U.S. Patent Application Publication No. 2018/0168627;

U.S. patent application Ser. No. 15/385,915, entitled FIRING MEMBER PIN ANGLE, U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, U.S. Patent Application Publication No. 2018/0168598;

U.S. patent application Ser. No. 15/385,922, entitled SURGICAL INSTRUMENT WITH MULTIPLE FAILURE RESPONSE MODES, U.S. Patent Application Publication No. 2018/0168622;

U.S. patent application Ser. No. 15/385,924, entitled SURGICAL INSTRUMENT WITH PRIMARY AND SAFETY PROCESSORS, U.S. Patent Application Publication No. 2018/0168624;

U.S. patent application Ser. No. 15/385,910, entitled ANVIL HAVING A KNIFE SLOT WIDTH, U.S. Patent Application Publication No. 2018/0168611;

U.S. patent application Ser. No. 15/385,903, entitled CLOSURE MEMBER ARRANGEMENTS FOR SURGICAL INSTRUMENTS, U.S. Patent Application Publication No. 2018/0168604;

U.S. patent application Ser. No. 15/385,906, entitled FIRING MEMBER PIN CONFIGURATIONS, U.S. Patent Application Publication No. 2018/0168607;

U.S. patent application Ser. No. 15/386,188, entitled STEPPED STAPLE CARTRIDGE WITH ASYMMETRICAL STAPLES, U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, U.S. Patent Application Publication No. 2018/0168643;

U.S. patent application Ser. No. 15/386,206, entitled STAPLE CARTRIDGE WITH DEFORMABLE DRIVER RETENTION FEATURES, U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, U.S. Patent Application Publication No. 2018/0168593;

U.S. patent application Ser. No. 15/385,894, entitled SHAFT ASSEMBLY COMPRISING A LOCKOUT, U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, U.S. Patent Application Publication No. 2018/0168596;

U.S. patent application Ser. No. 15/385,916, entitled SURGICAL STAPLING SYSTEMS, U.S. Patent Application Publication No. 2018/0168575;

U.S. patent application Ser. No. 15/385,918, entitled SURGICAL STAPLING SYSTEMS, U.S. Patent Application Publication No. 2018/0168618;

U.S. patent application Ser. No. 15/385,919, entitled SURGICAL STAPLING SYSTEMS, U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, U.S. Patent Application Publication No. 2018/0168621;

U.S. patent application Ser. No. 15/385,923, entitled SURGICAL STAPLING SYSTEMS, U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, U.S. Patent Application Publication No. 2015/0297233; and U.S. patent application Ser. No. 14/319,016, entitled FASTENER CARTRIDGE INCLUDING A LAYER ATTACHED THERETO, U.S. Patent Application Publication No. 2015/0297235.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATED SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical cutting and fastening instrument 10 that may or may not be reused. In the illustrated embodiment, the instrument 10 includes a housing 100 that comprises a handle 110 that is configured to be grasped, manipulated and actuated by the clinician. In the illustrated example, a dedicated shaft assembly 1000 is operably coupled to the handle 110. In alternative embodiments, however, the handle assembly is configured to be employed with a variety of different interchangeable shaft assemblies that each have a surgical end effector operably coupled thereto that is configured to perform one or more surgical tasks or procedures. For example, the interchangeable shaft assemblies disclosed herein may be employed with various robotic systems, instruments, components and methods disclosed in U.S. patent application Ser. No. 13/118,241, filed May 27, 2011, now U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

As the present Detailed Description proceeds, it will be understood that the various aspects of the shaft assembly 1000 may also be effectively employed in connection with robotically-controlled surgical systems. Thus, the term "housing" may also encompass a housing or similar portion of a robotic system that houses or otherwise operably supports or is otherwise associated with at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. In addition, various components may be "housed" or contained in the housing or various components may be "associated with" a housing. In such instances, the components may not be contained with the housing or supported directly by the housing.

The illustrated embodiment is an endoscopic instrument and, in general, the embodiments of the instrument 10 described herein are endoscopic surgical cutting and fastening instruments. It should be noted, however, that according to various embodiments, the instrument may be a non-endoscopic surgical cutting and fastening instrument, for example. Various surgical instruments are disclosed in U.S. Pat. No. 7,845,537, entitled SURGICAL INSTRUMENT HAVING RECORDING CAPABILITIES; U.S. Pat. No. 8,608,045, entitled POWERED SURGICAL CUTTING AND STAPLING APPARATUS WITH MANUALLY RETRACTABLE FIRING SYSTEM; and U.S. Pat. No. 9,050,083, entitled MOTORIZED SURGICAL INSTRUMENT, the entire disclosures of which are hereby incorporated by reference herein.

Figure 2:
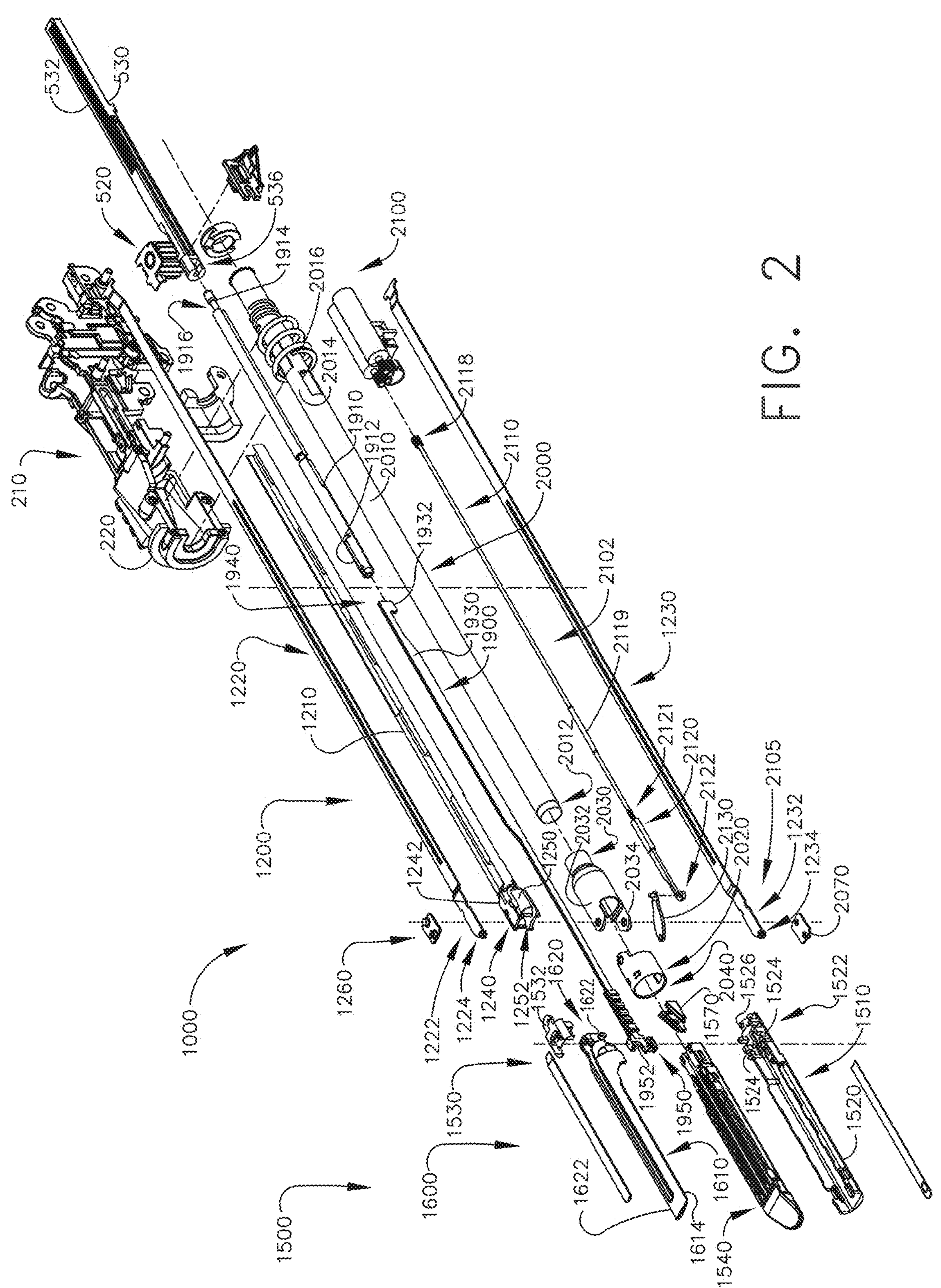
FIG. 2 is an exploded assembly view of a shaft assembly of the powered surgical stapling system of FIG. 1.

Turning to FIG. 2, in the illustrated example, the shaft assembly 1000 includes an end effector 1500 that is configured to cut and staple tissue. The end effector 1500 comprises a first jaw 1510 and a second jaw 1600 that is movably supported on the first jaw 1510. The first jaw comprises an elongated channel 1520 that is configured to operably support a surgical staple cartridge 1540 therein. The second jaw 1600 comprises an anvil 1610 that includes an elongated anvil body 1612 and an anvil mounting portion 1620. Alternative arrangements are contemplated, however, wherein the first jaw comprises an anvil and the second jaw comprises a surgical staple cartridge or a channel configured to support a surgical staple cartridge. In the illustrated example, the elongated anvil body 1612 includes a staple forming undersurface 1614 thereon that is adapted for confronting relationship with respect to the surgical staple cartridge 1540. The anvil 1610 is pivotally supported on or movably supported on the elongated channel 1520 by a pair of anvil trunnions 1622 that are formed on the anvil mounting portion 1620. Each trunnion 1622 is pivotally received in a corresponding trunnion cradle 1524 formed in a proximal end portion of the elongated channel 1520. The trunnions 1622 are pivotally retained within their respective cradles 1524 by an anvil retainer 1530.

Figure 3:
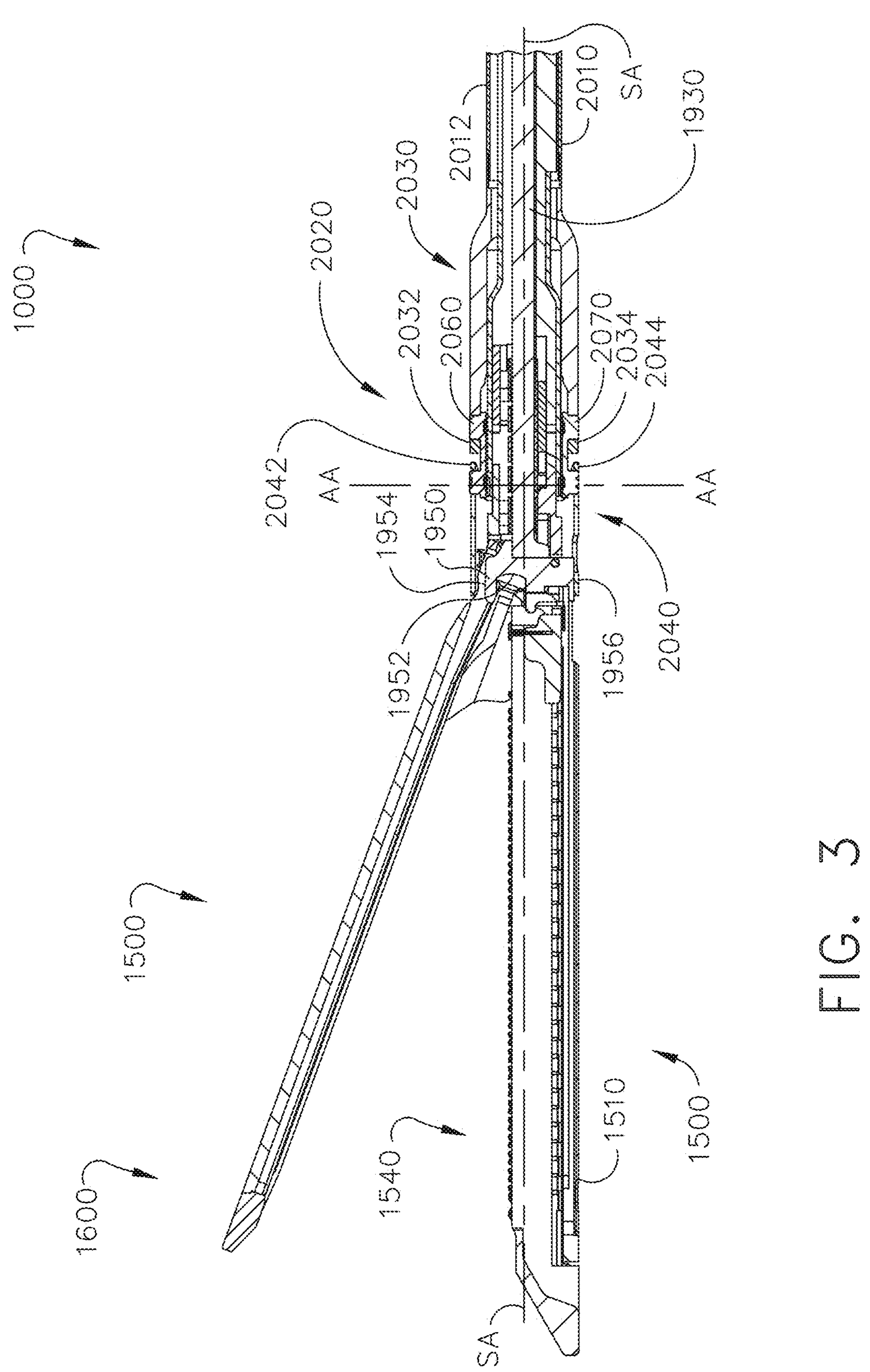
FIG. 3 is a cross-sectional view of a portion of the shaft assembly and a surgical end effector of the powered surgical stapling system of FIG. 1, with an anvil of the surgical end effector in an open position.

Still referring to FIG. 2, the shaft assembly 1000 includes a spine assembly 1200 that includes a spine shaft 1210 that is configured to, one, slidably support a firing member assembly 1900 therein and, two, slidably support a closure member assembly 2000 which extends around the spine assembly 1200. The spine assembly 1200 further includes upper and lower spine stays 1220 and 1230 that are supported by the spine shaft 1210. As can be seen in FIG. 2, a distal end 1212 of spine shaft 1210 terminates in an upper lug mount feature 1240 and in a lower lug mount feature 1250. The upper lug mount feature 1240 is formed with a lug slot 1242 therein that is adapted to mountingly support the distal end 1222 of the upper spine stay 1220 therein. Similarly, the lower lug mount feature 1250 is formed with a lug slot 1252 therein that is adapted to mountingly support the distal end 1232 of the lower spine stay 1230 therein. The distal end 1222 of the upper spine stay 1220 includes a pivot socket 1224 therein that is adapted to rotatably receive therein a pivot pin 1532 that is formed on a channel cap or anvil retainer 1530. The distal end 1232 of the lower spine stay 1230 includes lower pivot pin 1234 that adapted to be received within a pivot hole (not shown) formed in the proximal end portion 1522 of the elongated channel 1520. The lower pivot pin 1234 is vertically aligned with the pivot socket 1224 to define an articulation axis AA about which the surgical end effector 1500 may articulate relative to the shaft 1000. See FIG. 3.

In the illustrated arrangement, the closure member assembly 2000 comprises a proximal closure tube segment or closure member segment 2010. The proximal closure tube segment 2010 is operably coupled to a double pivot closure sleeve assembly 2020 that defines an articulation joint 2105 about which the end effector 1500 may articulate relative to the remaining portion of the shaft assembly 1000. Other shaft assemblies, however, may not be capable of articulation. As can be seen in FIG. 2, in one form, the double pivot closure sleeve assembly 2020 comprises an intermediate closure tube segment 2030 that is attached to a distal end 2012 of the proximal closure tube segment 2010. In addition, the double pivot closure sleeve assembly 2020 includes an end effector closure tube or distal closure tube 2040 that has upper and lower distally projecting tangs 2042, 2044. An upper double pivot link 2060 includes upwardly projecting distal and proximal pivot pins that engage respectively an upper distal pin hole in the upper proximally projecting tang 2042 and an upper proximal pin hole in an upper distally projecting tang 2032 on the intermediate closure tube segment 2030. A lower double pivot link 2070 includes upwardly projecting distal and proximal pivot pins that engage respectively a lower distal pin hole in the lower proximally projecting tang 2044 and a lower proximal pin hole in the lower distally projecting tang 2034. See FIGS. 2 and 3.

Figure 4:
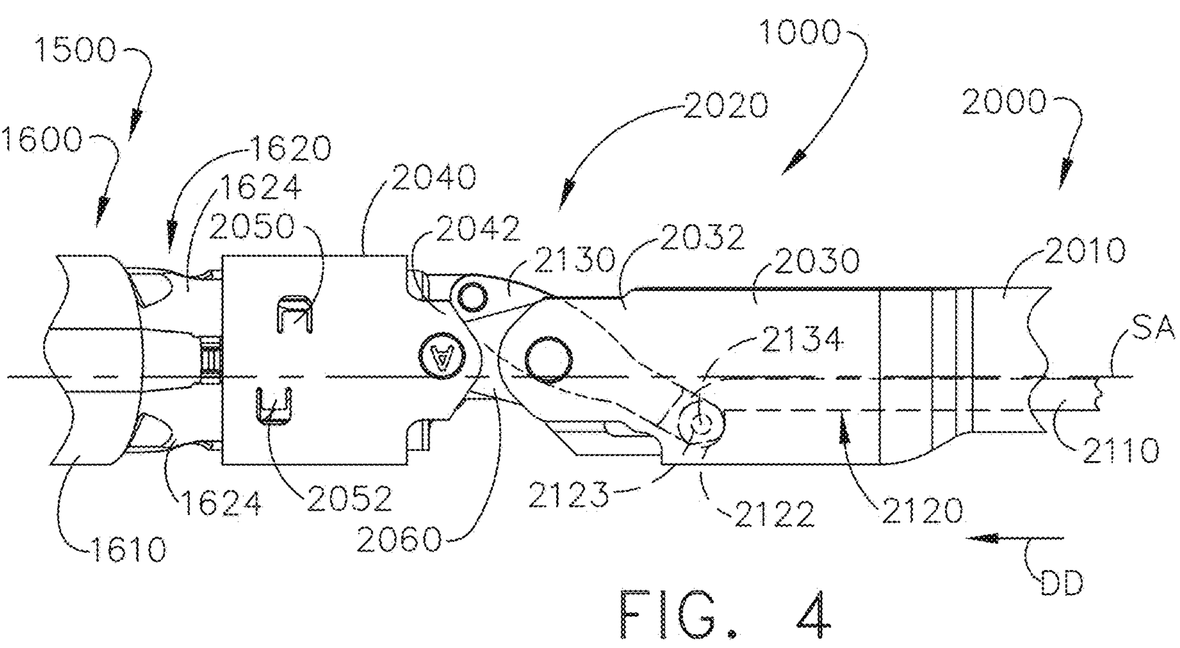
FIG. 4 is a top view of a portion of the shaft assembly and surgical end effector of FIG. 3 in an unarticulated position.
Figure 5:
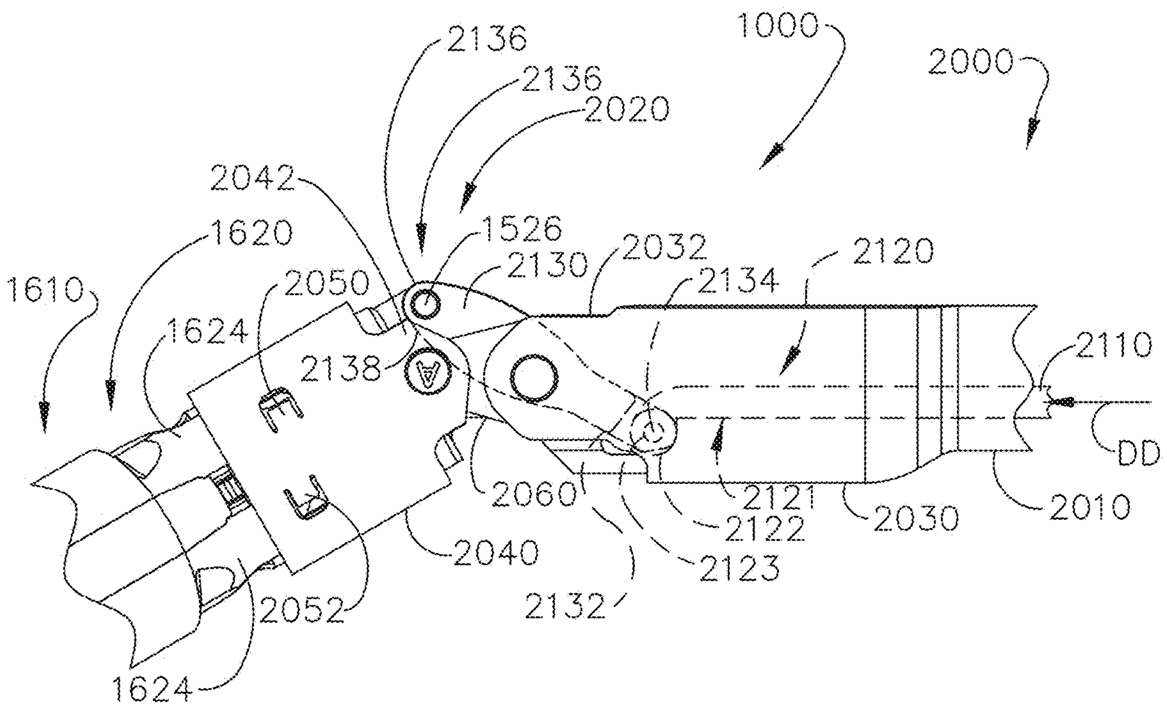
FIG. 5 is another top view of a portion of the shaft assembly and surgical end effector of FIG. 3 in an articulated position.

As will be discussed in further detail below, the anvil 1610 is moved from an open position to a closed position by translating the closure member assembly 2000 in the distally (direction "DD"). The anvil 1610 is opened by proximally translating the closure member assembly 2000 which causes the end effector closure sleeve 2020 to interact with the anvil 1610 and pivot it to an open position. Referring to FIGS. 4 and 5, in at least one arrangement, the distal closure member or end effector closure tube 2040 employs two axially offset, proximal and distal positive jaw opening features 2050 and 2052. In FIGS. 4 and 5, the proximal positive jaw opening feature 2050 is located on the right side (as viewed by a user of the tool assembly) of the shaft axis SA. The positive jaw opening features 2050, 2052 are configured to interact with corresponding relieved areas (not shown) and stepped portions (not shown) that are formed on the anvil mounting portion 1620 as described in further detail in U.S. patent application Ser. No. 15/635,631, filed Jun. 28, 2017, entitled SURGICAL INSTRUMENT WITH AXIALLY MOVABLE CLOSURE MEMBER, the entire disclosure which has been herein incorporated by reference as well as in other references incorporated herein. Other jaw opening arrangements may also be employed.

In the illustrated example as well as other anvil configurations disclosed in references incorporated herein, the anvil mounting portion 1620 has a cam surface or cam surfaces 1624 formed thereon. As the end effector closure tube 2040 is moved distally, a cam surface formed on a distal end of the end effector closure tube 2040 interacts with the cam surfaces 1624 on the anvil mounting portion 1620 to cam the anvil 1610 into a closed position.

As was also indicated above, the shaft assembly 1000 further includes a firing member assembly 1900 that is supported for axial travel within the spine shaft 1210. The firing member assembly 1900 includes an intermediate firing shaft portion 1910 that is configured for attachment to a distal cutting portion or knife bar 1930. The intermediate firing shaft portion 1910 may include a longitudinal slot 1912 in the distal end thereof which can be configured to receive a tab 1932 on the proximal end of the distal knife bar 1930. The longitudinal slot 1932 and the proximal end tab 1932 can be sized and configured to permit relative movement therebetween and can comprise a slip joint 1940. The slip joint 1940 can permit the knife bar 1930 to move axially relative to the intermediate firing shaft portion 1910 to accommodate articulation of the end effector 1500, for example. The knife bar 1930 includes a knife portion 1950 that includes a blade or tissue cutting edge 1952 and includes an upper anvil engagement tab 1954 and lower channel engagement tabs 1956. Various firing member configurations and operations are disclosed in various other references that are incorporated herein by reference.

In the illustrated example, the surgical end effector 1500 is selectively articulatable about the articulation axis AA by an articulation drive system 2100. In one form, the articulation drive system 2100 includes proximal articulation driver 2110 that is operably coupled to an intermediate articulation driver 2120 that is pivotally coupled to a distal articulation link 2130. As can be most particularly seen in FIGS. 4 and 5, an offset attachment lug 2122 is formed on a distal end of the intermediate articulation driver 2120. A pivot hole 2123 is formed in the offset attachment lug 2122 and is configured to pivotally receive therein a proximal link pin 2134 formed on the proximal end 2132 of the distal articulation link 2130. A distal end 2136 of the articulation link 2120 includes a pivot hole 2138 that is configured to pivotally receive therein a channel pin 1526 that is formed on the proximal end portion 1522 of the elongated channel 1520. Thus, axial movement of intermediate articulation driver 2120 will thereby apply articulation motions to the elongated channel 1520 to thereby cause the surgical end effector 1500 to articulate about the articulation axis AA relative to the spine assembly 1200.

Figure 6:
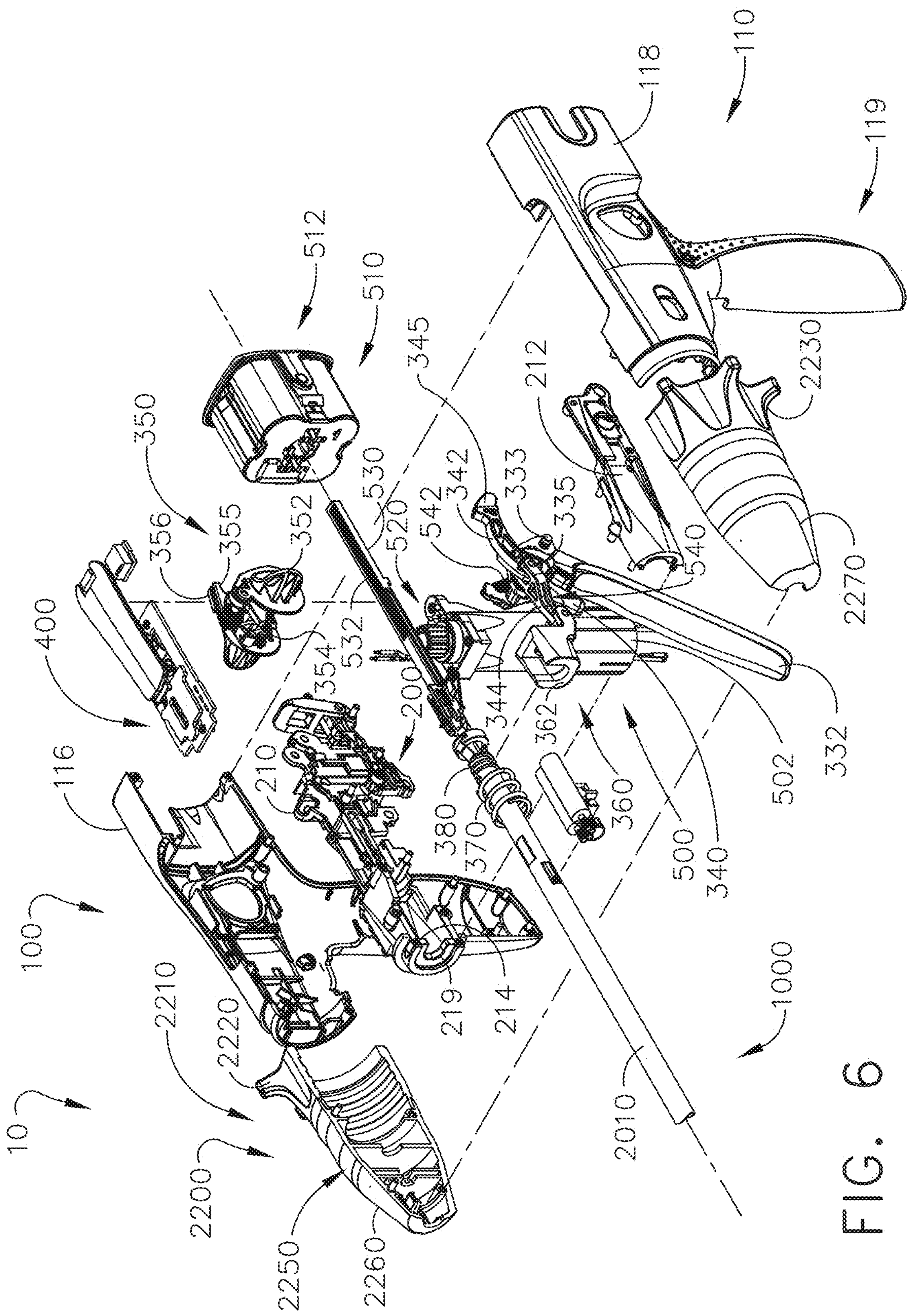
FIG. 6 is an exploded assembly view of a handle or housing of the powered surgical stapling system of FIG. 1.
Figure 7:
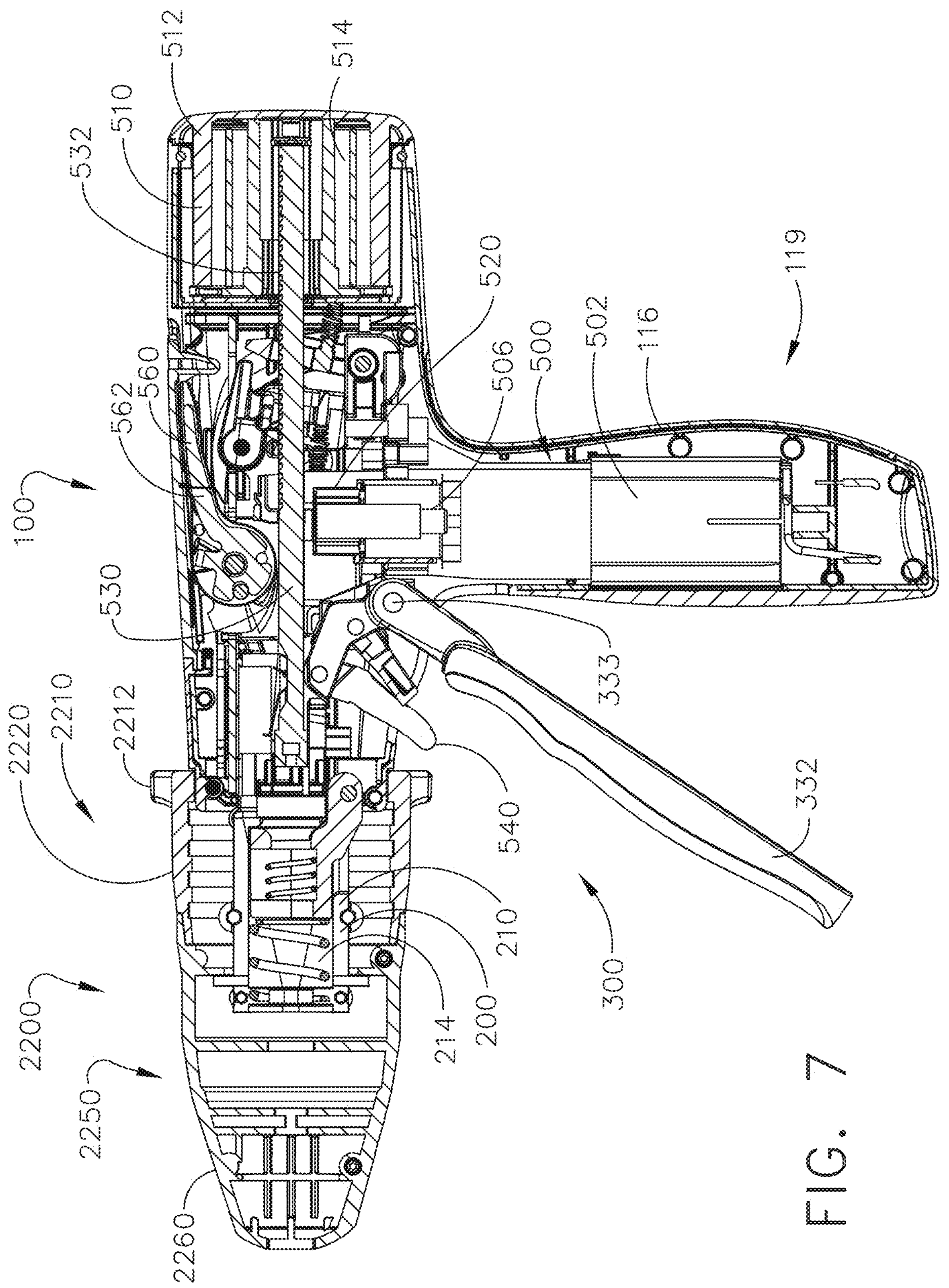
FIG. 7 is a cross-sectional view of the handle of FIG. 6 with portions of the shaft assembly omitted for clarity.

Turning now to FIGS. 6 and 7, the handle 110 comprises handle housing segments 116, 118 cooperate to form a pistol grip portion 119 that can be gripped and manipulated by the clinician. As will be discussed in further detail below, the handle 110 operably supports a plurality of drive systems therein that are configured to generate and apply various control motions to the shaft assembly 1200. Referring now to FIG. 2, the handle 110 may further include a frame assembly or chassis 200 that operably supports a plurality of drive systems. For example, the frame assembly 200 can operably support a "first" or closure drive system, generally designated as 300, which may be employed to apply closing and opening motions to the end effector 1500 of the shaft assembly 1000. In the illustrated example, the frame assembly 200 includes a right frame portion 210 and a frame cap 212 that is attached thereto by snap features, lugs, screws, etc. to define a shuttle cavity 214 therein. See FIGS. 6 and 7.

In at least one form, the closure drive system 300 may include an actuator in the form of a closure trigger 332 that is pivotally supported by the frame assembly 200. More specifically, as illustrated in FIGS. 6 and 7, the closure trigger 332 is pivotally coupled to the frame assembly 200 by a pin 333. Such arrangement enables the closure trigger 332 to be manipulated by a clinician such that when the clinician grips the pistol grip portion 119 of the handle 100, the closure trigger 332 may be easily pivoted from a starting or "unactuated" position to an "actuated" position and more particularly to a fully compressed or fully actuated position. The closure trigger 332 may be biased into the unactuated position by spring or other biasing arrangement. In various forms, the closure drive system 300 further includes a closure linkage assembly 340 that is pivotally coupled to the closure trigger 1032. As can be seen in FIG. 6, the closure linkage assembly 340 may include a first closure link 342 and a second closure link 344 that are each pivotally coupled to the closure trigger 332 by a pin 335.

Still referring to FIG. 6, it can be observed that the first closure link 342 may have a locking wall or end 345 thereon that is configured to cooperate with a closure release assembly 350 that is pivotally coupled to the right frame portion 210. In at least one form, the closure release assembly 350 may comprise a release button assembly 352 that has a distally protruding locking pawl 354 formed thereon. The release button assembly 352 may be pivoted in a counterclockwise direction by a release spring (not shown). As the clinician depresses the closure trigger 332 from its unactuated position towards the pistol grip portion 119 of the handle 100, the first closure link 342 pivots upward to a point wherein the locking pawl 354 drops into retaining engagement with the locking wall 345 on the first closure link 344 thereby preventing the closure trigger 332 from returning to the unactuated position. Thus, the closure release assembly 350 serves to lock the closure trigger 332 in the fully actuated position. When the clinician desires to unlock the closure trigger 332 to permit it to be biased to the unactuated position, the clinician simply pivots the closure release button assembly 352 such that the locking pawl 354 is moved out of engagement with the locking wall 345 on the first closure link 344. When the locking pawl 354 has been moved out of engagement with the first closure link 344, the closure trigger 332 may pivot back to the unactuated position. Other closure trigger locking and release arrangements may also be employed.

In the illustrated example, an arm 355 extends from the closure release button 352. A magnetic element 356, such as a permanent magnet, for example, may be mounted to the arm 355. When the closure release button 352 is rotated from its first position to its second position, the magnetic element 356 can move toward a circuit board 400. The circuit board 400 can include at least one sensor that is configured to detect the movement of the magnetic element 356. In at least one embodiment, for example, a "Hall Effect" sensor (not shown) can be mounted to the bottom surface of the circuit board 400. The Hall Effect sensor can be configured to detect changes in a magnetic field surrounding the Hall Effect sensor that are caused by the movement of the magnetic element 356. The Hall Effect sensor can be in signal communication with a microcontroller, for example, which can determine whether the closure release button 352 is in its first position, which is associated with the unactuated position of the closure trigger 332 and the open configuration of the end effector, its second position, which is associated with the actuated position of the closure trigger 332 and the closed configuration of the end effector, and/or any position between the first position and the second position.

Figure 8:
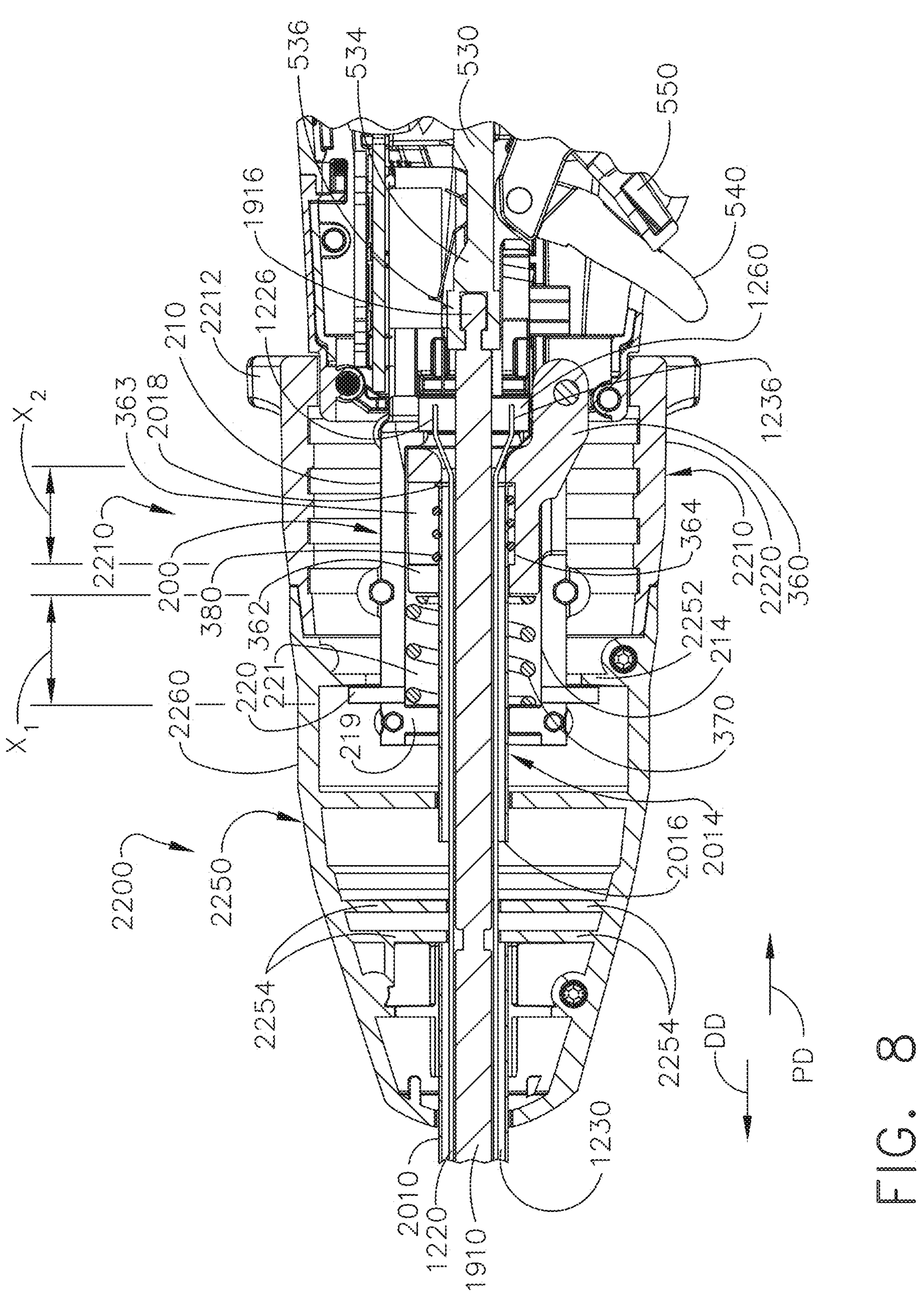
FIG. 8 is an enlarged cross-sectional view of the handle and shaft assembly of FIG. 7.

In at least one form, the handle 100 and the frame assembly 200 operably support another drive system referred to herein as a firing drive system 500 that is configured to apply firing motions to the firing member assembly 1900 in the shaft assembly 1000. The firing drive system 500 may also be referred to herein as a "second drive system". The firing drive system 500 may employ an electric motor 502 that is located in the pistol grip portion 119 of the handle 100. In various forms, the motor 502 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 502 may be powered by a power source 510 that in one form may comprise a removable power pack 512. As can be seen in FIG. 8, for example, the power pack 512 may support a plurality of batteries 514 therein. Batteries 514 may each comprise, for example, a Lithium Ion ("LI") or other suitable battery. The power pack 512 is configured for removable operable attachment to the circuit board assembly 400 which is also operably coupled to the motor 502. A number of batteries 514 may be connected in series may be used as the power source for the surgical instrument 10. In addition, the power source 510 may be replaceable and/or rechargeable.

As outlined above with respect to other various forms, the electric motor 502 can include a rotatable shaft 506 that operably interfaces with a gear reducer assembly 520 that is mounted in meshing engagement with a with a set, or rack, of drive teeth on a longitudinally-movable drive member 530. An attachment lug 1916 is formed on a proximal end 1914 of the intermediate firing shaft portion 1910. The attachment lug 1916 is configured to be received within an attachment cradle 536 that is formed in a distal end of the longitudinally movable drive member 530. In use, a voltage polarity provided by the power source 510 can operate the electric motor 502 in a clockwise direction wherein the voltage polarity applied to the electric motor by the battery can be reversed in order to operate the electric motor 502 in a counter-clockwise direction. When the electric motor 502 is rotated in one direction, the drive member 530 will be axially driven in the distal direction "DD". When the motor 502 is driven in the opposite rotary direction, the drive member 530 will be axially driven in a proximal direction "PD". The handle 100 can include a switch which can be configured to reverse the polarity applied to the electric motor 502 by the power source 510. As with the other forms described herein, the handle 100 can also include a sensor that is configured to detect the position of the drive member 530 and/or the direction in which the drive member 530 is being moved.

Actuation of the motor 502 can be controlled by a firing trigger 540 that is pivotally supported on the handle 100. The firing trigger 540 may be pivoted between an unactuated position and an actuated position. The firing trigger 540 may be biased into the unactuated position by a spring 542 or other biasing arrangement such that when the clinician releases the firing trigger 540, it may be pivoted or otherwise returned to the unactuated position by the spring or biasing arrangement. In at least one form, the firing trigger 540 can be positioned "outboard" of the closure trigger 332 as was discussed above. In at least one form, a firing trigger safety button 550 may be pivotally mounted to the closure trigger 332. The safety button 550 may be positioned between the firing trigger 540 and the closure trigger 332 and have a pivot arm protruding therefrom. When the closure trigger 332 is in the unactuated position, the safety button 550 is contained in the handle 100 where the clinician cannot readily access it and move it between a safety position preventing actuation of the firing trigger 540 and a firing position wherein the firing trigger 540 may be fired. As the clinician depresses the closure trigger 332, the safety button 550 and the firing trigger 540 pivot down wherein they can then be manipulated by the clinician.

As indicated above, in at least one form, the longitudinally movable drive member 530 has a rack of teeth formed thereon for meshing engagement with a corresponding drive gear of the gear reducer assembly 520. At least one form also includes a manually-actuatable "bailout" assembly 560 that is configured to enable the clinician to manually retract the longitudinally movable drive member 530 should the motor 502 become disabled. See FIG. 7. The bailout assembly 560 may include a lever or bailout handle assembly 562 that is configured to be manually pivoted into ratcheting engagement with teeth 532 also provided in the drive member 530. Thus, the clinician can manually retract the drive member 530 by using the bailout handle assembly 562 to ratchet the drive member 530 in the proximal direction PD. U.S. patent application Ser. No. 12/249,117, filed Oct. 10, 2008, now U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

One method of attaching the shaft assembly 1000 to the handle will now be described with reference to FIGS. 6-9. In the illustrated example, the shaft assembly 1000 includes a nozzle assembly 2200 that includes a proximal nozzle assembly 2210 and a distal nozzle assembly 2250. The proximal nozzle assembly 2210 includes a right proximal nozzle segment 2220 and a left proximal nozzle segment 2230. The proximal nozzle segments 2220, 2230 may be attached together by snap lugs, screws, adhesive, etc. The distal nozzle assembly 2250 includes a right distal nozzle segment 2260 and a left distal nozzle segment 2270. The right distal nozzle segment 2260 and the left distal nozzle segment 2270 are coupled together by snap features, lugs, screws, adhesive, etc. The proximal nozzle assembly 2210 and the distal nozzle assembly 2250 may be attached together by adhesive, friction, etc. The nozzle assembly 2200 is journaled on the housing 100 for selective rotation relative thereto about the shaft axis SA. In the illustrated example, the distal nozzle assembly 2250 is provided with an inwardly extending proximal mounting flange 2252 that interfaces with a frame mounting flange 220 formed on frame portion 210 of the frame assembly 200. The proximal nozzle assembly 2210 is formed with fins 2212 to facilitate rotation of the nozzle assembly 2200 about the shaft axis SA.

In the illustrated arrangement, the shaft assembly 1000, including the end effector 1500 attached thereto, is rotatable about the shaft axis SA by rotating the nozzle assembly 2200 relative to the handle 100. As can be seen in FIG. 8, for example, the distal nozzle assembly 2250 includes a shaft engagement flange 2254 that extends inwardly through nozzle engagement openings 2016 in a proximal end portion 2014 of the proximal closure tube segment 2010. Such arrangement permits the shaft assembly 1000 to be rotated about the shaft axis SA when the clinician rotates the nozzle assembly 2200. The nozzle engagement openings 2016 are sized to permit axial movement of the proximal closure tube segment 2010 relative to the shaft engagement flange 2254. Still referring to FIG. 8, the distal nozzle assembly 2250 may further include a support sleeve portion 2256 configured to movably support the proximal closure tube segment 2010 therein. In addition, as can be seen in FIG. 9, a proximal end 1226 of the upper spine stay 1220 and a proximal end 1236 of the lower spine stay 1230 are each supported in a spine bearing 1260 that is rotatably supported in the frame assembly 200.

Figure 9:
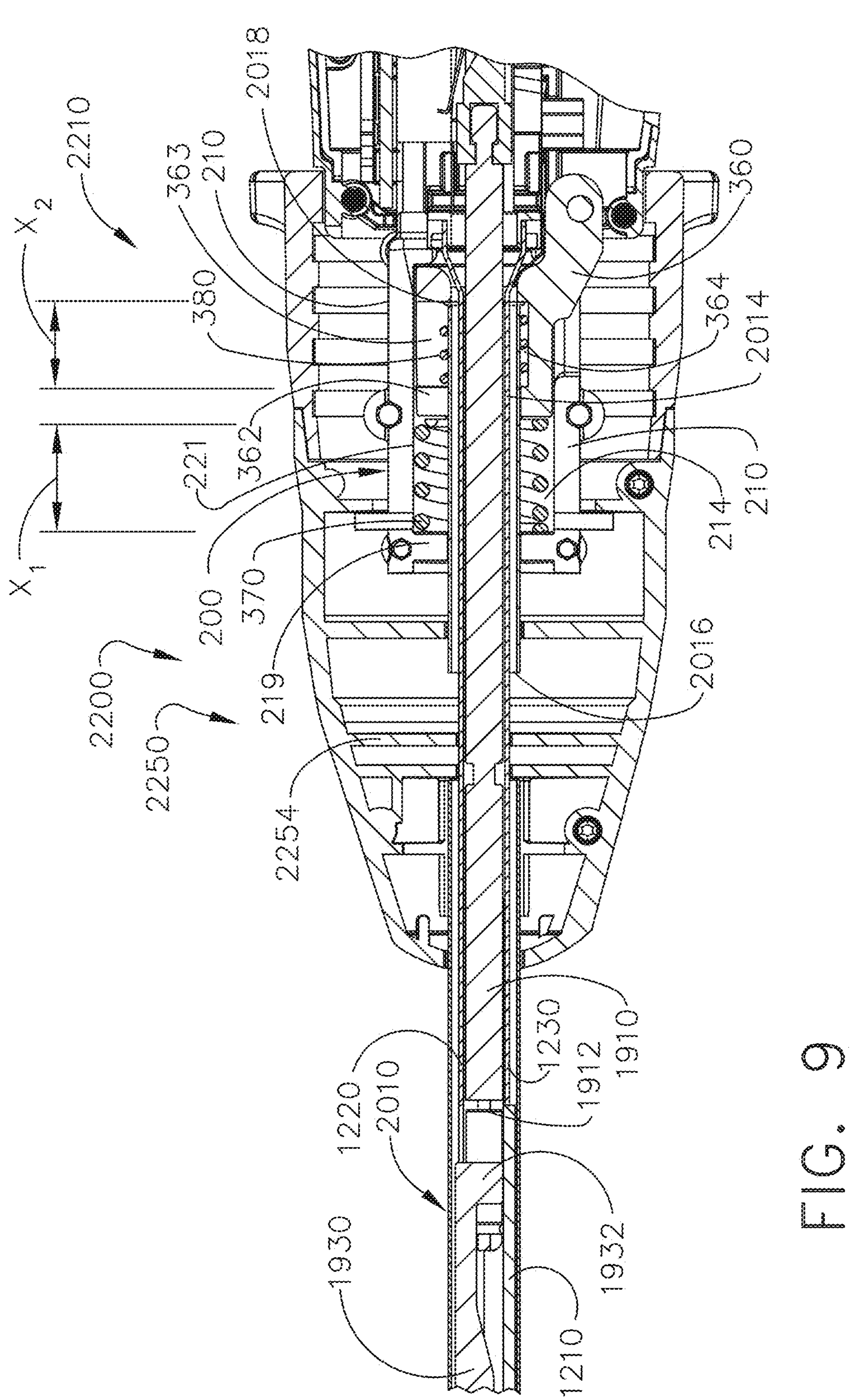
FIG. 9 is another enlarged cross-sectional view of the handle and shaft assembly of FIG. 7.

Referring now to FIGS. 6, 8 and 9, the proximal end portion 2014 of the proximal closure tube segment 2010 is movably supported in a closure shuttle 360 that is linked to the second closure link 344 of the closure linkage assembly 340 (FIG. 6). The closure shuttle 360 is slidably supported in the shuttle cavity 214 in the fame assembly 200. The proximal end portion 2014 of the proximal closure tube segment 2010 extends through a U-shaped cradle opening 362 in the closure shuttle 360 to be rotatably supported therein. Such arrangement permits the proximal end portion 2014 of the proximal closure tube segment 2010 to rotate relative to the closure shuttle 360 when the shaft assembly 1000 is rotated relative to the handle 100. In addition, when the clinician depresses the closure trigger 332, the closure shuttle is moved in the distal direction DD within the shuttle cavity 214 and also causes the closure member assembly 2000 in the distal direction to apply closure motions to the end effector 1500.

As can be seen in FIGS. 8 and 9, a first spring 370 is journaled on the proximal portion 2014 of the proximal closure tube segment 2010 between the cradle wall 362 of the closure shuttle 360 and a distal end wall 219 formed on the right frame portion 210 (first spring space 221). The axial length of the first spring space is designated $X_1$. The first spring 370 biases the closure shuttle 360 proximally (arrow PD) into the starting position that corresponds to a fully open position of the anvil. See FIG. 10. In the illustrated example, a proximal flange 2018 is formed on the proximal end portion 2014 of the proximal closure tube segment 2010. The proximal flange 2018 is configured to slidably travel within a closure or second cavity 364 that is formed in the closure shuttle 360 as shown. The axial length of the second cavity or second spring space 363 is designated as $X_2$. In at least one arrangement, for example, $X_1 > X_2$. A second closure spring or biasing member 380 is located within the second spring space 363 to bias the proximal flange 2018 on the proximal closure tube segment 2010 in the distal direction DD against the cradle wall 362 of the closure shuttle 360.

During the initial clamping of the target tissue between the anvil 1610 and the surgical staple cartridge 1540, the closure drive system 300 must apply a sufficient amount of axial closure force to the anvil 1610 to pivot the anvil 1610 to a closed position and retain it in that position throughout the staple forming process. The term "closure procedure" in at least one application refers to the process of moving the anvil from a fully opened position to a closed position on the target tissue and retaining the anvil in the closed position until the staple forming process has been fully completed and the anvil is ready to be reopened to release the target tissue from the end effector. The amount of closure force required to close the anvil and retain it in a closed position can vary during the stapling process due to "tissue creep". For example, as the anvil compresses the target tissue, fluid within the clamped target tissue can "creep" or migrate within the tissue and even flow to adjacent unclamped tissue. Further tissue creep may be experienced as the knife portion 1950 is driven through the clamped target tissue. Thus, tissue creep can also affect the amount of firing force required to cut the target tissue and fire the staples within the staple cartridge. As the knife portion 1950 nears the end of its stroke, the amount of required firing force may be reduced because the creeping fluid has completed the migration into the adjacent unclamped tissue.

Figure 10:
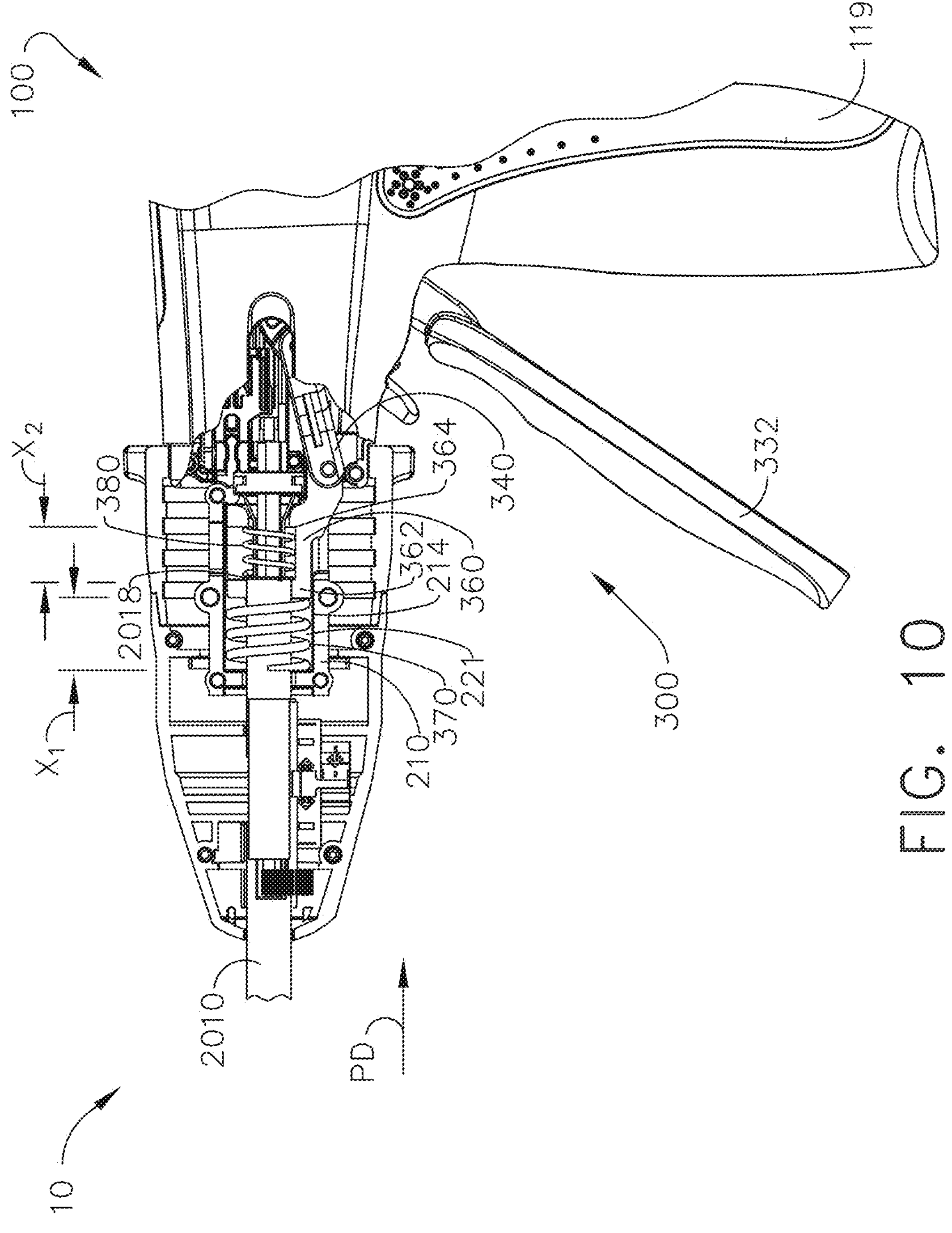
FIG. 10 is another side cross-sectional view of the handle and shaft assembly of FIG. 7 in a position that results in the jaws of the surgical end effector being oriented in an open position.
Figure 11:
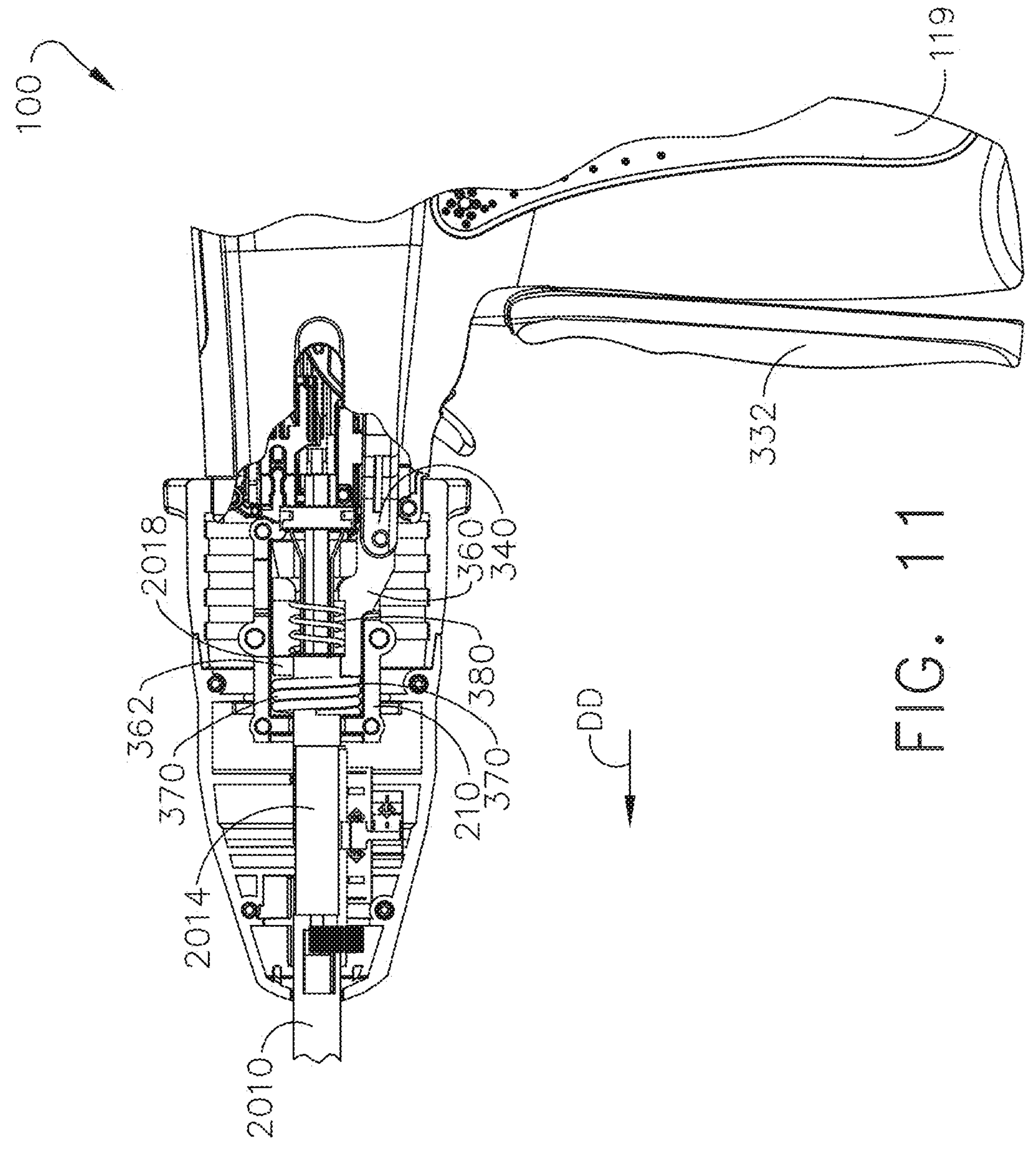
FIG. 11 is another side cross-sectional view of the handle and shaft assembly of FIG. 7 in a position that results in the closure of the end effector jaws.

FIG. 10 illustrates the closure drive system 300 in an unactuated orientation. As can be seen in FIG. 10, the first spring 370 has biased the closure shuttle 360 proximally in the PD direction within the shuttle cavity 214 in the frame assembly 200 to its proximal-most or starting position. As a result of the closure shuttle 360 being attached to the closure trigger 332 by the closure linkage assembly 340, the closure trigger 332 is pivoted into the unactuated starting position. When the closure drive system 300 is in that unactuated position, the anvil 1610 is in a fully open position. In at least one example, the first spring 370 is "weaker" than the second spring 380. Stated another way, the second spring 380 is stiffer than the first spring 370. That is the spring constant $K_1$ of the first spring 370 is less than the spring constant $K_2$ of the second spring 380. Thus, $K_2 > K_1$. In some arrangements, for example, $K_2$ may be up to ten times greater than $K_1$. In other arrangements $K_2/K_1 > 1$. In alternative arrangements $K_2 < K_1$. The clinician initiates the closure process by depressing the closure trigger 332 towards the pistol grip 119 of the housing 100. This action starts to move the closure shuttle 360 in the distal direction DD which starts to compress the first spring 370. As the closure shuttle 360 starts moving distally, the closure shuttle 360 also starts moving the proximal closure tube segment 2010 distally. As the proximal closure tube segment 2010 moves distally, the entire closure member assembly 2000 (of which the proximal closure tube segment 2010 is a part) moves distally to apply closure motions to the anvil 1610. As the clinician continues to pivot the closure trigger 332 toward the pistol grip 119, the closure shuttle 360 continues to move distally and compresses the first spring 370. As the anvil 1610 starts to close, the amount of closure forces required may begin to increase as the anvil 1610 begins to compress the target tissue. As the target tissue begins to compress, the fluids contained therein may begin to creep within the target tissue which can directly affect the amount of closure forces required to completely close the anvil. As the resistance to closure increases, the closure member assembly 2000 can move in the proximal direction PD against the closure force applied by the second spring 380 to the proximal closure tube segment 2010. FIG. 11 depicts the closure drive system 300 in a fully closed position that corresponds to a fully closed position of the anvil 1610. Thus, the ultimate amount of closure force applied to the anvil 1610 through the closure member assembly 2000 can vary due to the ability of the second spring 380 to compress in response to the closure resistance experienced by the anvil during the closure procedure. Thus, the anvil can "progressively close" as it experiences changes in the amount of resistance created by the target tissue. This may also be referred to herein as generating a "progressive closure force".

Once the jaws 1510, 1600 are closed onto the target tissue and locked in that position, the clinician may then institute the firing process by depressing the firing trigger 540 which causes the knife bar 1910 to drive the knife portion 1950 through the clamped target tissue. As the knife portion 1950 is driven distally through the end effector 1500, the knife blade 152 cuts through the target tissue. In addition, in at least one arrangement, the knife portion 1950 engages and distally drives a camming assembly, sometimes referred to as a wedge sled 1970 that is slidably supported in the surgical staple cartridge 1540. As the wedge sled 1970 is driven distally through the staple cartridge 1540, the cams formed on the wedge sled 1970 camming engage staple drivers (not shown) that are movably supported within the staple cartridge 1540. Each staple driver may support one or more surgical staples thereon. The staple drivers are commonly supported in axially lines located on each side of an elongated slot that is formed in the staple cartridge. As the wedge sled 1570 contacts the staple drivers, they are driven upward (toward the closed anvil) 1610 thereby driving the staple(s) supported thereon through the target tissue and into forming contact with the staple forming undersurface 1614 of the anvil body 1612. The wedge sled 1570 is position distal to the tissue cutting knife blade, so the staples are deployed through the target tissue before the target tissue is cut.

Further, as the knife portion 1950 is driven through the target tissue, tabs or flanges formed in the knife portion engage the anvil 1610 as well as the elongated channel 1510 and retain the anvil 1610 and channel 1510 closed and spaced at a desired spacing arrangement during the stapling process. While such distal advancement of the knife portion may reduce the amount of closure force required from the closure system, a significant amount of "firing forces" must be generated by the firing system to push the knife portion 1950 through the target tissue and to overcome the resistive forces and friction of the system as the wedge sled actuates the staple drivers. Thus, the firing system must be able to generate sufficient firing forces and the firing system components must be sufficiently robust to effectively accommodate such forces while also being flexible enough to accommodate articulation of the end effector. These design requirements of the closure and firing systems may also be exacerbated by the type and composition of the target tissue. Further, the components of these systems must be sufficiently small enough to be inserted through the small cannulas of trocars.

Figure 12:
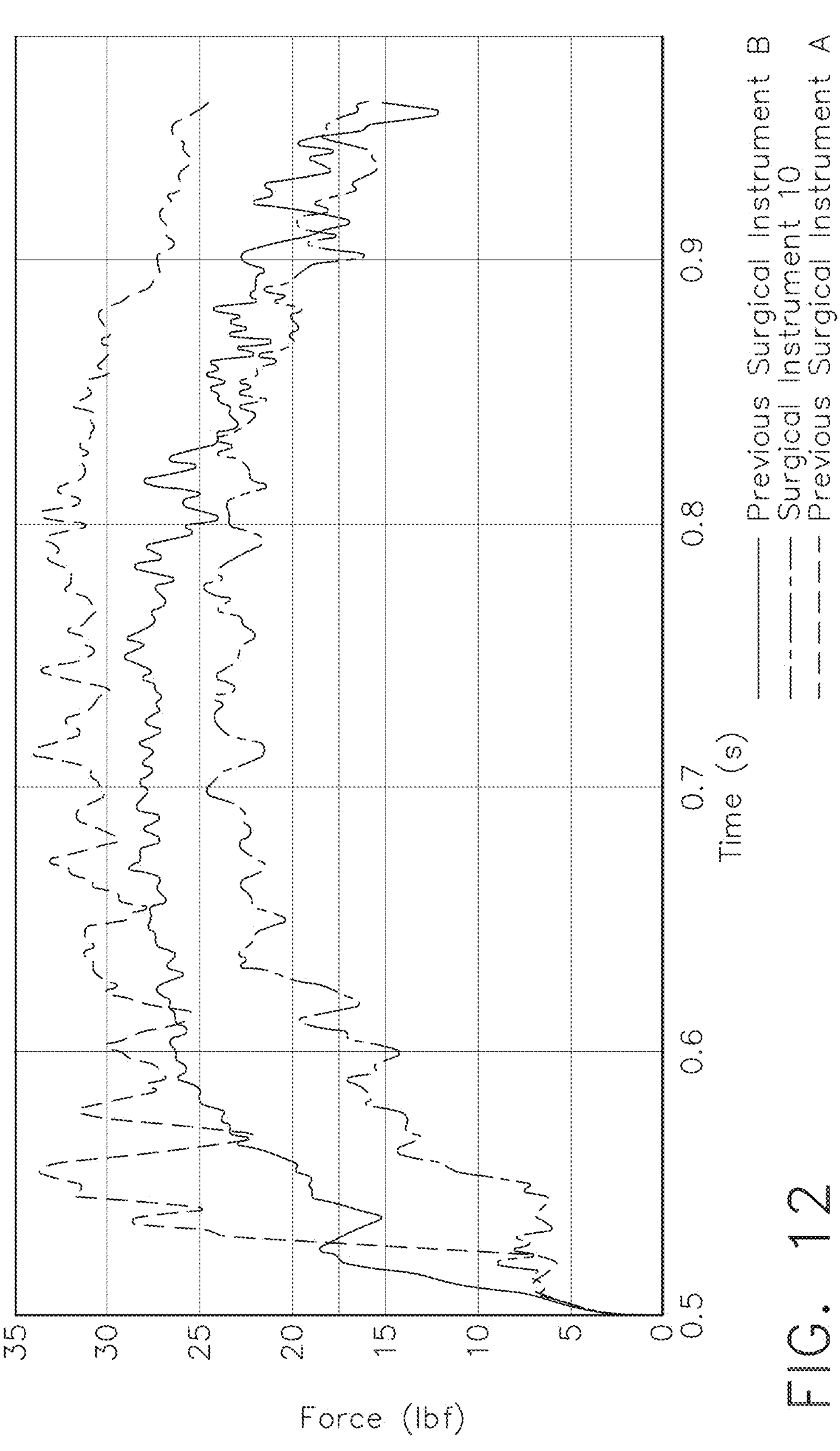
FIG. 12 is a graphical comparison of closure forces between a surgical instrument embodiment that employs a progressive closure drive system and two previous surgical instruments that employ different closure drive system arrangements.

FIG. 12 is a graphical comparison between a the surgical instrument 10 that employs the progressive closure drive system 300 described above and two previous surgical instruments A and B that employ different closure drive arrangements. Previous surgical instrument A employs a closure drive system that is directly linked to the closure actuator or closure trigger. While previous surgical instrument A does employ a spring for biasing the closure system to an unactuated position, previous surgical instrument A does not employ a second biasing member like surgical instrument 10 described above. In addition, the anvil of surgical instrument A lacks a camming surface or surfaces like anvil 1610 described above. Instead, the anvil of surgical instrument A has a hard edge that is arranged for contact by the closure member or tube. As the closure member contacts that hard edge, the anvil is pivoted closed.

Still referring to FIG. 12, previous surgical instrument B is similar in some aspects to previous surgical instrument A in that surgical instrument B has a first biasing member for biasing the closure system to an unactuated position. However, surgical instrument B does not employ a second biasing member like instrument 10 described above. The anvil of surgical instrument B, however, does employ camming surfaces that are configured to be contacted by the closure member to pivot the anvil to a closed position. FIG. 12 is a plot showing the amount of time to complete the closure procedure vs the amount of closure forces required during the procedure for each of the three surgical instruments: surgical instrument 10, surgical instrument A and surgical instrument B. As can be seen in FIG. 12, the amount of closure forces required throughout the closure procedure for surgical instrument 10 is less than the closure forces required by surgical instruments A and B. While the closure forces needed by surgical instrument B are less than the closure forces required by surgical instrument A, the closure forces required by surgical instrument 10 are considerably less than the closure forces required by both A and B throughout the closure process.

Figures 13A, 13B:
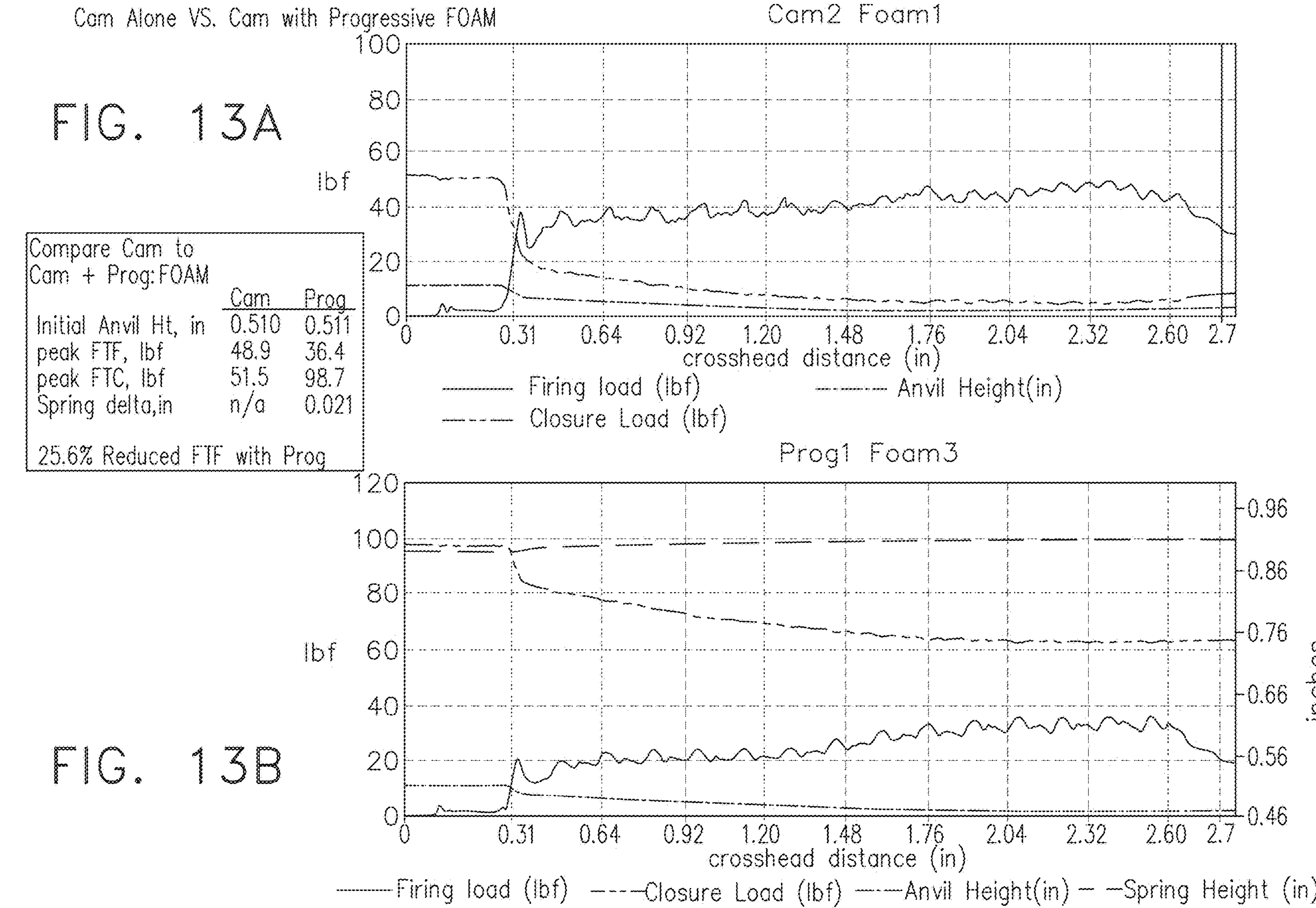
FIG. 13A is a graphical depiction of a force to fire (FTF) and a force to close (FTC) experienced by a previous surgical instrument embodiment that employs camming surfaces on an anvil thereof as a firing member or knife thereof travels through the anvil from a proximal-most starting position to a distal-most ending position in the anvil (crosshead distance in inches)
FIG. 13B is a graphical depiction of a force to fire (FTF) and a force to close (FTC), anvil height and spring height experienced by a surgical instrument embodiment that employs a progressive closure drive system.

FIGS. 13A and 13B compare the force to fire (FTF), the force to close (FTC) experienced by surgical instrument 10 and surgical instrument B (with the camming surfaces on the anvil) as the firing member or knife travels through the anvil from a proximal-most starting position to a distal-most ending position in the anvil (crosshead distance). FIG. 13A illustrates the FTF, FTC and the anvil height during the firing procedure for the surgical instrument B. FIG. 13B illustrates the FTF, FTC, anvil height and spring height of surgical instrument 10. As can be seen from reference to FIGS. 13A and 13B, the initial anvil height for surgical instrument B was 0.0510 inches and the initial anvil height for surgical instrument 10 was 0.511 inches. The peak closure force FTC in pounds for surgical instrument B was 51.5 pounds and for surgical instrument 10 was 98.7 pounds. The peak FTF in pounds for surgical instrument B was 48.9 pounds and for surgical instrument 10 was 36.4 pounds. Thus, surgical instrument 10 experienced a 25.6% reduction in the amount of closure forces required by surgical instrument 10. This reduction in the amount of firing force required may allow the firing system components to be fabricated from lighter and or smaller component arrangements.

Figure 14:
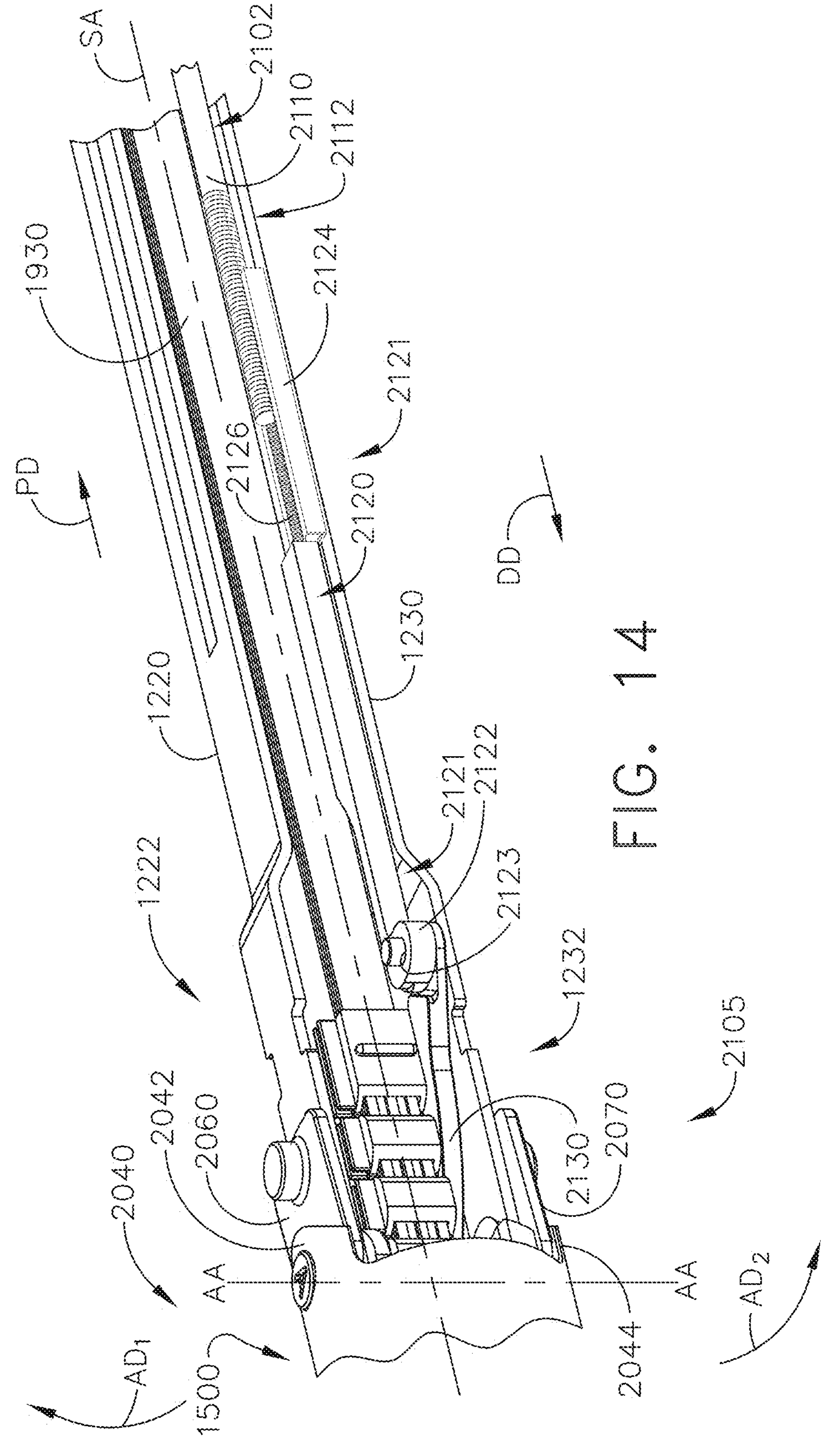
FIG. 14 is a partial perspective view of a portion of a shaft assembly.

As indicated above, the surgical instrument 10 includes an articulation drive system 2100 that is configured to selectively articulate the surgical end effector 1500 relative to the shaft assembly 1000 about an articulation axis AA that is transverse to the shaft axis SA. See FIG. 14. The articulation drive system 2100 includes an articulation drive assembly 2102 that comprises a proximal articulation driver 2110 that is coupled to an intermediate articulation driver 2120 that is pivotally coupled to a distal articulation link 2130 that is attached to the proximal end of the elongated channel 1520. See FIG. 2. In one example, the distal articulation link 2130 is attached to the intermediate articulation driver 2120 on one side of the shaft axis SA. The distal articulation link 2130 is attached to the elongated channel 1520 on the opposite side of the shaft axis SA so that the distal articulation link 2130 extends transversely across the shaft axis SA. In the illustrated example, the joint between the proximal articulation driver 2110 and the intermediate articulation driver 2120 may also function as an articulation lock assembly 2121 that serves to retain the surgical end effector 1500 in an articulated position after the articulation motion applied to the proximal articulation driver 2110 is discontinued. In the illustrated example, a distal end 2112 of the proximal articulation driver 2110 is threaded. The threaded distal end 2112 of the proximal articulation driver 2110 is in threaded engagement with a threaded socket 2126 in a proximal end 2124 of the intermediate articulation driver 2120. Rotation of the proximal articulation driver 2110 in a first rotary direction will cause the intermediate articulation driver 2120 to axially move in a first or distal direction DD. Movement of the intermediate articulation driver 2120 in the distal direction DD will cause the surgical end effector 1500 to pivot about the articulation axis AA in a first articulation direction $AD_1$. Rotation of the proximal articulation driver in a second rotary direction will cause the intermediate articulation driver 2120 to move in a second or proximal direction PD. Axial movement of the intermediate articulation driver 2120 in the proximal direction PD will cause the surgical end effector 1500 to pivot about the articulation axis AA in a second articulation direction $AD_2$.

Figure 15:
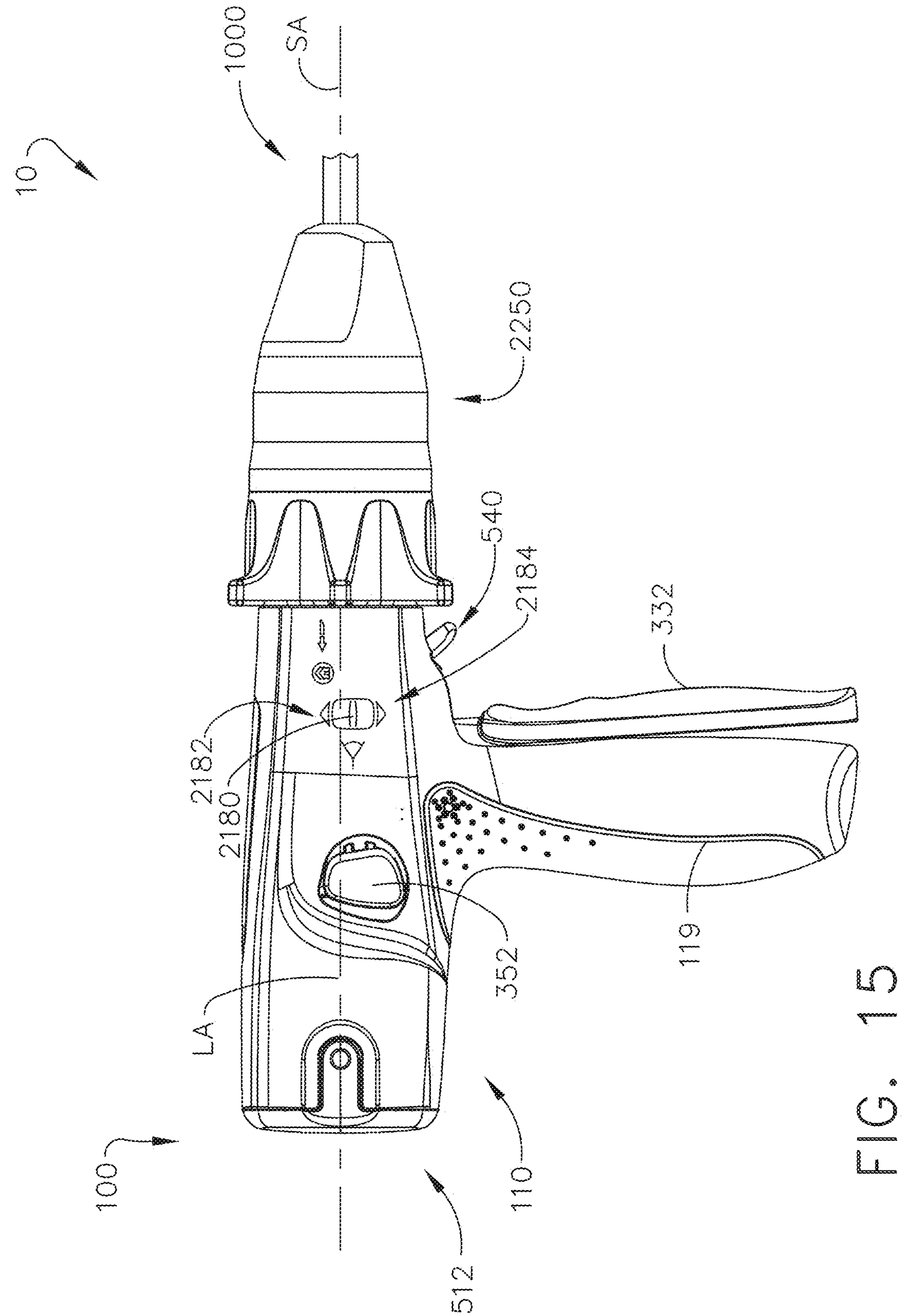
FIG. 15 is a side elevational view of a portion of another powered surgical instrument.
Figure 16:
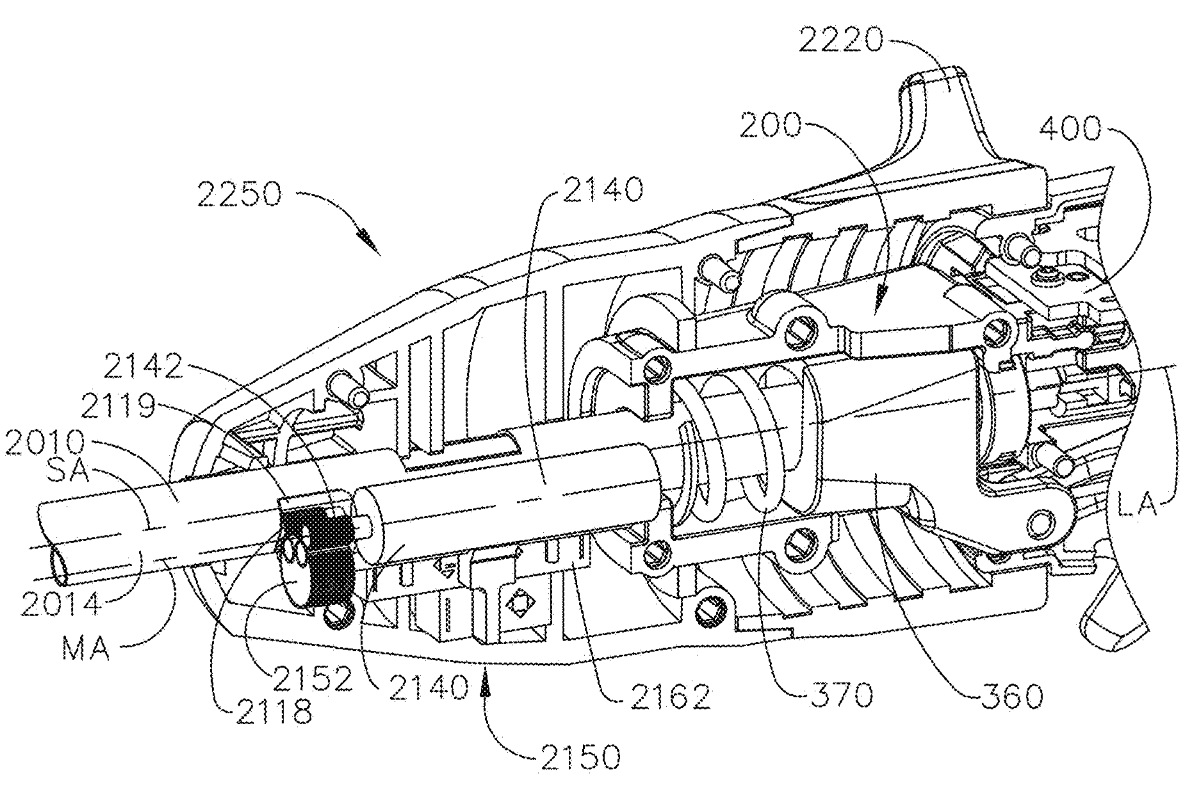
FIG. 16 is a partial perspective view of a portion of the powered surgical instrument of FIG. 15, with portions thereof omitted for clarity.
Figure 17:
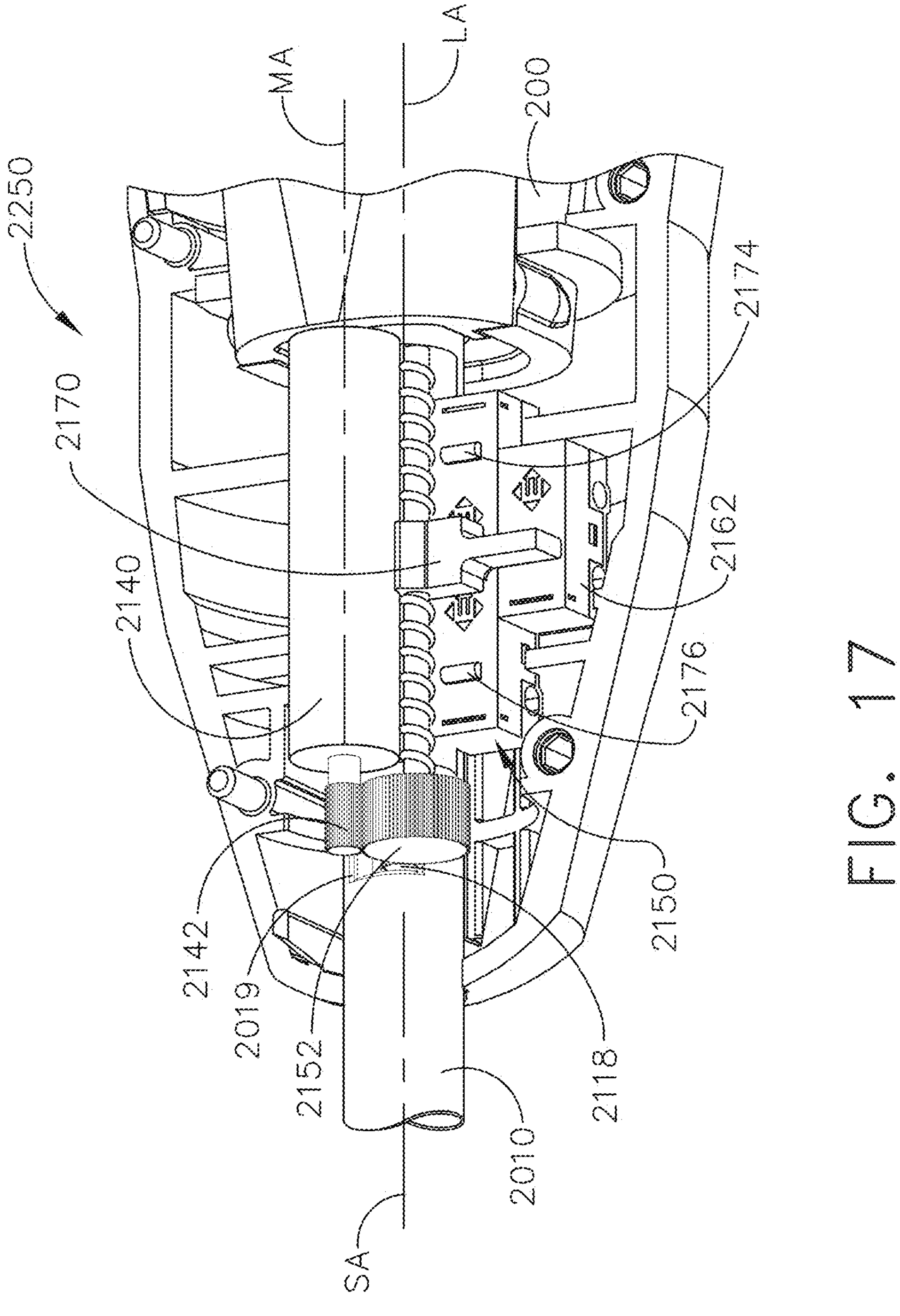
FIG. 17 is another partial perspective view of a portion of the powered surgical instrument of FIG. 15, with portions thereof omitted for clarity.
Figure 18:
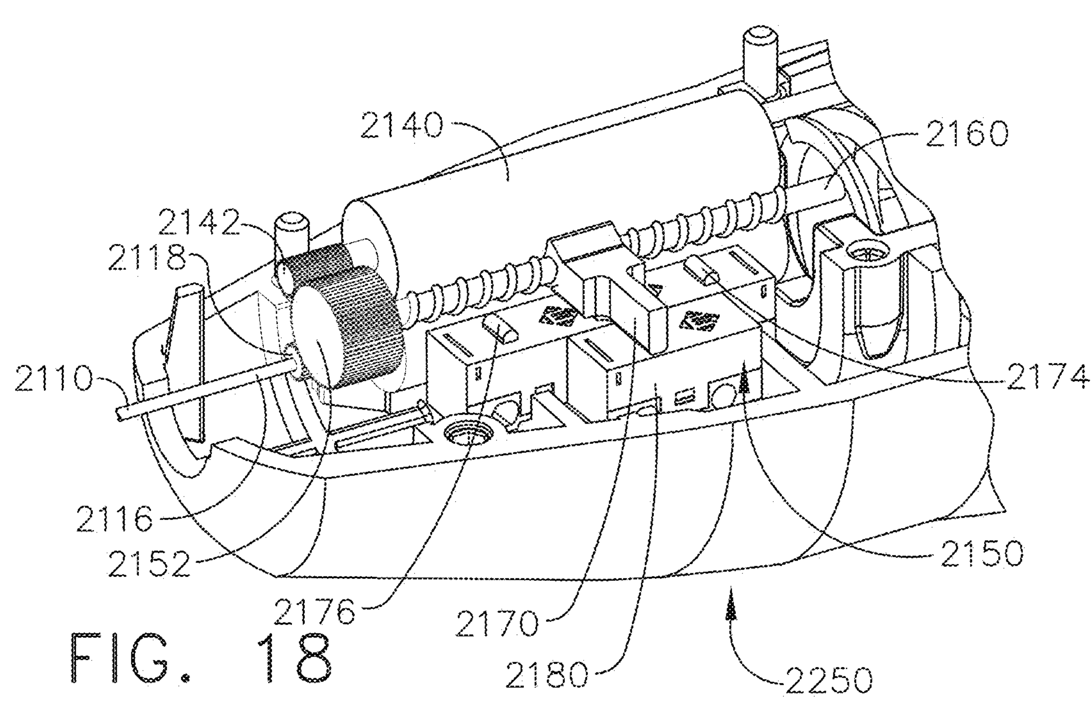
FIG. 18 is another partial perspective view of a portion of the powered surgical instrument of FIG. 15, with portions thereof omitted for clarity.
Figure 19:
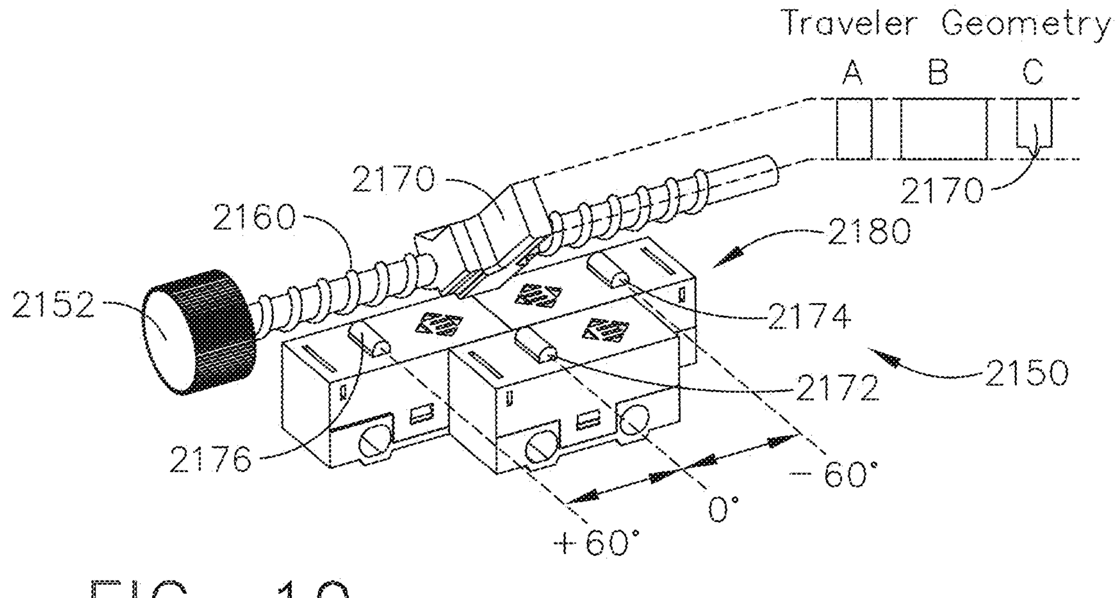
FIG. 19 is a perspective view of a motor switch system of the powered surgical instrument of FIG. 15, with portions thereof omitted for clarity.

In the illustrated example, housing 100 or handle 110 defines a longitudinal axis LA. See FIGS. 15 and 16. As indicated above, the shaft assembly 1000 also defines a shaft axis SA. The shaft axis SA and the longitudinal axis LA may be coaxial. The longitudinal the articulation drive system 2100 includes an articulation motor 2140 that is mounted within a distal nozzle assembly 2250 for rotational travel therewith in an orbit about the longitudinal axis LA when the user rotates the nozzle assembly 2250 relative to the housing 100. The distal nozzle assembly 2250 may also be referred to herein as a "shaft rotator assembly" that is configured to rotatably couple the shaft assembly 1000 to the housing 100. In one arrangement, the articulation motor 2140 includes a gear configuration that includes a motor output gear 2142. The motor output gear 2142 rotates about motor axis MA that is parallel to and offset from the longitudinal axis LA. See FIG. 16. In the illustrated example, the motor output gear 2142 is in meshing engagement with a control switch gear 2152 of a motor switch system 2150. The control switch gear 2152 is in meshing engagement with a proximal articulation drive gear 2118 that is formed on a proximal end 2116 of the proximal articulation driver 2110. Thus, rotation of the motor output gear 2142 in one direction will result in rotation of the proximal articulation driver 2110 in the first direction which will cause the intermediate articulation driver 2120 in the distal direction and cause the surgical end effector 1500 to articulate in the first articulation direction $AD_1$. Likewise rotation of the articulation motor in an opposite rotary direction will cause the proximal articulation driver 2110 to rotate in a second rotary direction and thereby cause the intermediate articulation driver 2120 to move in the proximal direction PD. Movement of the intermediate articulation driver 2120 in the proximal direction PD will cause the surgical end effector 1500 to articulate in the second articulation direction $AD_2$. In various embodiments, the articulation motor 2140 and gear configuration may, for example, be less than 12 mm in diameter and less than 1.5 inches long. The articulation motor 2140 may be of a brushed design with less than 1.5 watt power output. In at least some embodiments, the power output of the motor 2140 is approximately 0.75-1.0 watts. The gear configuration may be supported by the motor housing or it may be separate from the motor housing. In at least one example, the gear configuration has a 100:1 reduction although gear configurations with higher reduction ratios may be employed. In alternative arrangements, other motor configurations may be employed.

With respect to the articulation lock 2121, the threads on the distal end 2112 of the proximal articulation driver 2110 may, for example, comprise a #2 screw thread with either a fine (e.g., 64 threads/inch) or a coarse (less than 64 threads/inch) provides sufficient mechanical advantage for the articulation motor 2140 to cause articulation of the surgical end effector 1500 while also functioning as a lock to prevent movement of the surgical end effector 1500 after the articulation motor 2140 has been de-energized. As can also be seen in FIG. 2, the proximal articulation driver 2110 may be provided with a support shoulder portion 2119 that has a larger diameter than the adjacent portions of the of the proximal articulation driver 2110. The larger shoulder 2119 slidably interfaces with the spine shaft 1210 for additional support when in the locked position.

Figures 20, 21, 22:
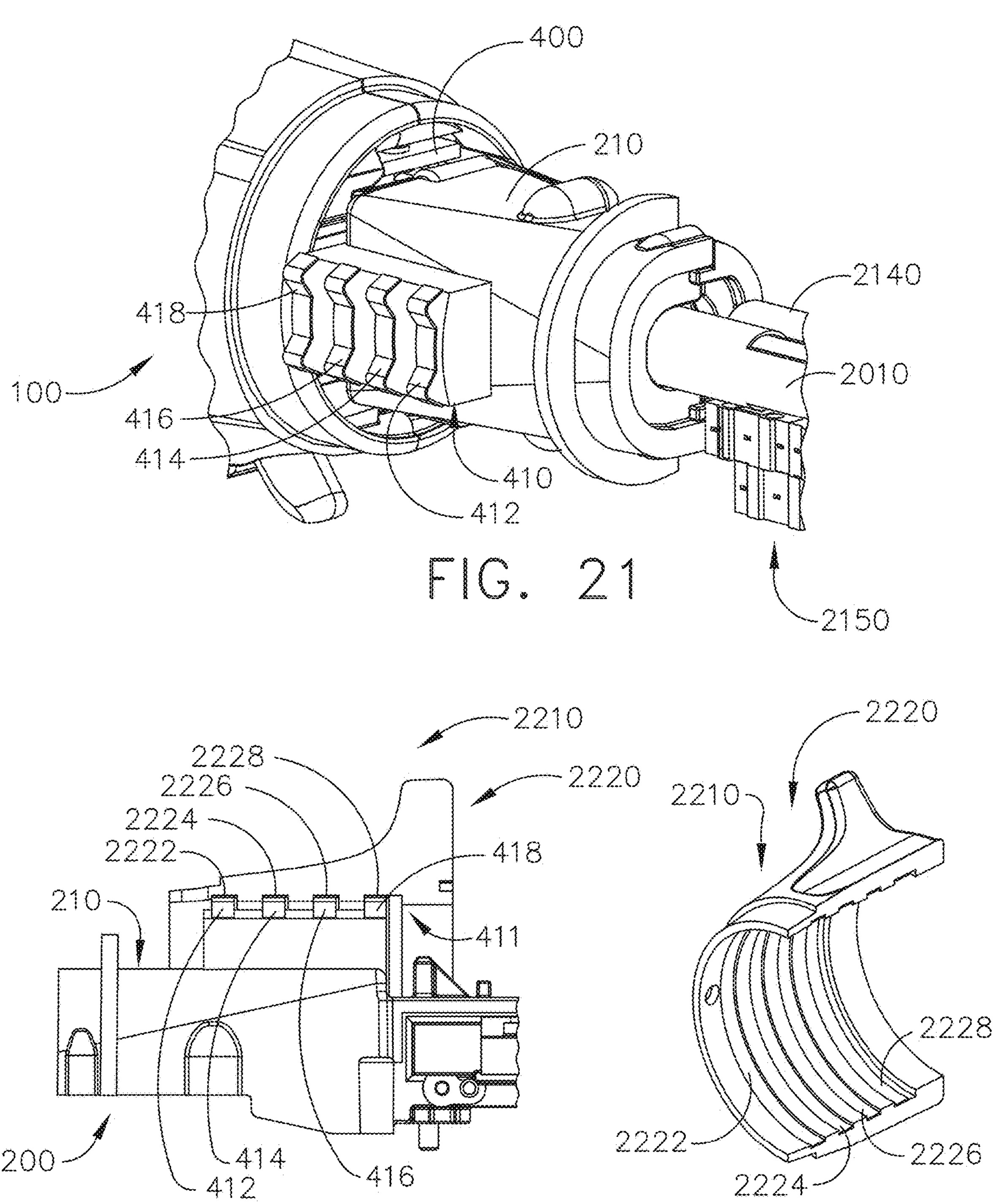
FIG. 20 is a perspective view of a proximal nozzle segment or fin segment of a nozzle assembly of the powered surgical instrument of FIG. 15.
FIG. 21 is a partial perspective view of portions of the powered surgical instrument of FIG. 15 with a distal nozzle portion omitted for clarity.
FIG. 22 is a side elevational view of portions of a chassis portion and a proximal nozzle segment of the powered surgical instrument of FIG. 15 with portions of the nozzle assembly thereof omitted for clarity.
Figures 23, 24, 25, 26:
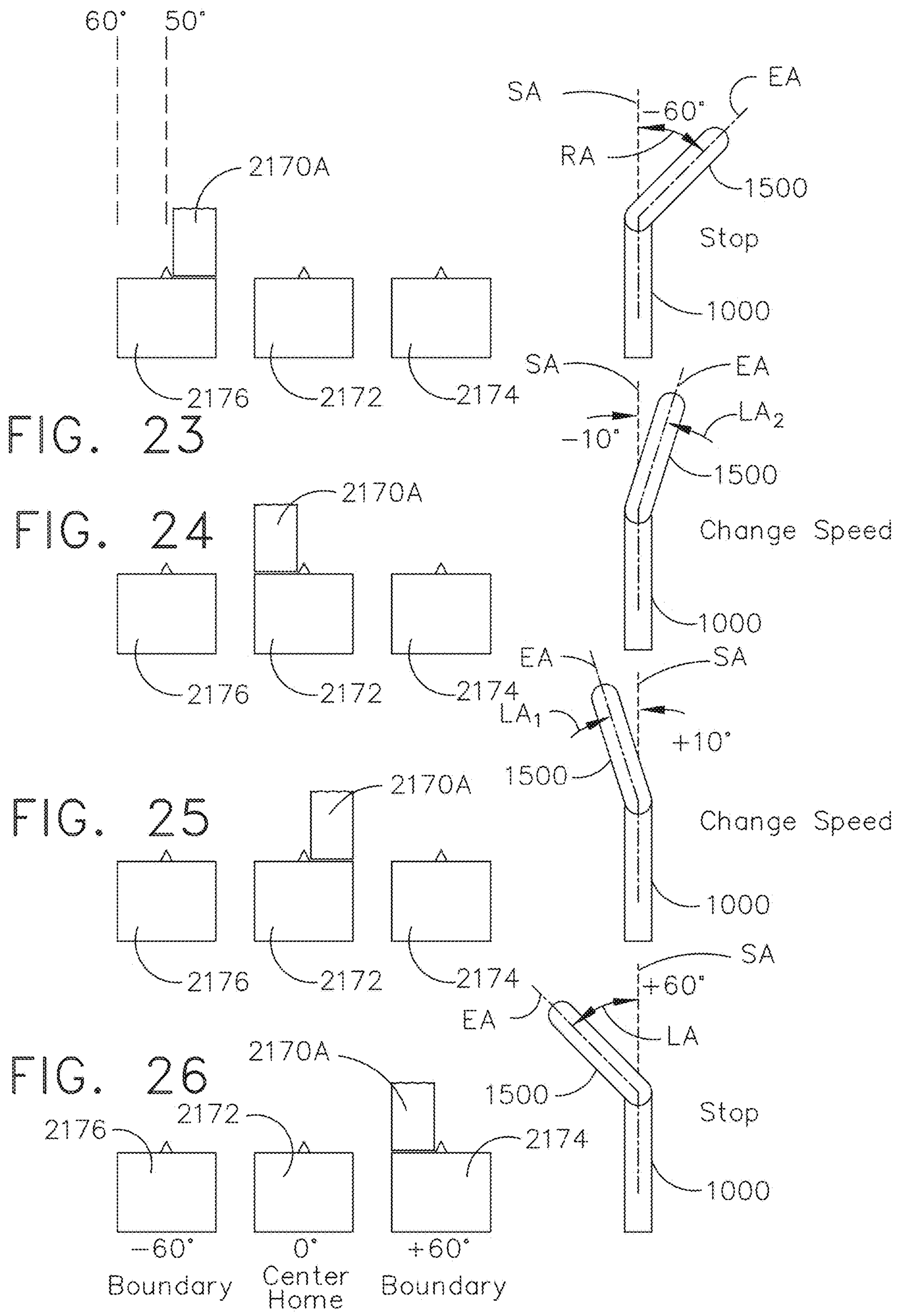
FIG. 23 is a graphic depiction of positions of switches of the switch system of FIG. 19 relative to a position of a switch traveler thereof in relation to an articulated position of an end effector of the powered surgical instrument of FIG. 15.
FIG. 24 is another graphic depiction of positions of switches of the switch system of FIG. 19 relative to another position of the switch traveler in relation to an articulated position of the end effector of the powered surgical instrument of FIG. 15.
FIG. 25 is another graphic depiction of positions of switches of the switch system of FIG. 19 relative to another position of the switch traveler in relation to an articulated position of the end effector of the powered surgical instrument of FIG. 15.
FIG. 26 is another graphic depiction of positions of switches of the switch system of FIG. 19 relative to another position of the switch traveler in relation to an articulated position of the end effector of the powered surgical instrument of FIG. 15.

Still referring to FIGS. 16-19, the motor switch system 2150 includes a switch traveler 2170 that is threaded onto a switch drive screw 2160 that is attached to the control switch gear 2152. Rotation of the motor output gear 2142 will cause the control switch gear 2152 to rotate which ultimately causes the switch drive screw 2160 to rotate. Rotation of the switch driver screw 2160 results in the axial movement of the switch traveler 2170 relative to a switch housing 2162 mounted in the distal nozzle assembly 2250. The switch housing 2162 operably supports a plurality of limit switches that are in communication with the control circuit board 400 that is supported in or otherwise associated with the housing 100 as will be further discussed below. See FIG. 16. In the illustrated example, three limit switches are employed: a central limit switch 2172, a proximal limit switch 2174 and a distal limit switch 2176. The switches 2172, 2174, 2176 are wired to a series of circuit traces or conductors 2222, 2224, 2226, 2228 that are mounted within the proximal nozzle assembly 2210. See FIG. 20. Circuit traces 2222, 2224, 2226 and 2228 are wired or electrically coupled to the articulation motor 2140 and switches 2172, 2174, 2176 by wires or flexible circuit conductors (not shown). Turning to FIGS. 21 and 22, a contact block 410 is fixedly mounted to the frame assembly 200 and includes contacts 412, 424, 416 and 418 that correspond respectively to circuit traces 2222, 2224, 2226 and 2228. Contacts 412, 414, 416, 418 are wired to the control circuit board 400. As the proximal nozzle assembly 2210 is rotated relative to the housing 100 about the shaft axis SA, power/control signals may be provided between the control circuit board 400 and the articulation motor 2140 and switches 2172, 2174, 2176 through a slip joint assembly 411 which comprises the circuit traces 2222, 2224, 2226, 2228 and contacts 412, 414, 416, 418 to facilitate rotation of the articulation motor 2140 and the control switch assembly relative to the housing 100 about the shaft axis SA. Articulation control switches 2180 are mounted on each side of housing 100 and are used to control the rotation of the articulation motor 2140. See FIG. 15. Switches 2180 may comprise "rocker-type" switches that, when depressed in one direction (arrow 2182), the articulation motor 2140 rotates the motor output gear 2142 in one rotary direction and when a switch 2180 is depressed in an opposite direction (arrow 2184) the articulation motor rotates the motor output gear 2142 in an opposite rotary direction.

Turning now to FIGS. 19 and 23-26, the positions of switches 2172, 2174, 2176 relative to the path of the switch traveler 2170 serve to define the range of articulation of the surgical end effector 1500. Switch 2172 comprises the central or home switch that corresponds to the unarticulated position of the surgical end effector 1500. When in that position, a central end effector axis EA is generally aligned with the shaft axis SA. When in this position, for example, the end effector 1500 may be inserted through or removed from a trocar cannula. Switch 2174 corresponds to a −60° left articulation boundary and switch 2176 corresponds to a +60° right articulation boundary. The −60° left articulation boundary may also be referred to herein as a "first maximum articulated position" of the surgical end effector 1500 located on a "first side" or left side of the shaft axis SA. The left −60° angle (LA in FIG. 26) may also be referred to as a "first maximum articulation angle" and comprises the angle between the end effector axis EA and the shaft axis SA when the surgical end effector 1500 is in the first maximum articulated position. Similarly, the +60° right articulation boundary may also be referred to herein as a "second maximum articulated position" of the surgical end effector 1500 located on a "second side" or right side of the shaft axis SA. The right +60° angle (RA in FIG. 23) may also be referred to as a "second maximum articulation angle" and comprises the angle between the end effector axis EA and the shaft axis SA when the surgical end effector 1500 is in the second maximum articulated position. Thus, in the illustrated example, the positions of switches 2174 and 2176 establish the maximum articulation positions for each articulation direction (left and right). In alternative arrangements, only two switches (2174, 2176) may be employed. The switches 2172, 2174, 2176 may comprise mechanical switches, Hall Effect switches, etc.

In at least one example, the central home switch 2172 may also be used to slow the articulation motor 2140 down prior to crossing the home or unarticulated position to allow the user to more easily determine when the end effector 1500 is aligned with the shaft assembly 1000 which would facilitate removable through a trocar, for example.

In one example, the geometric shape of the switch traveler in the region that is configured to engage the switches 2172, 2174, 2176 is selected to have a width such that it engages the switches at "X" degrees from home and is able to remain in contact with the switch from =X degrees to −X degrees. In at least one example, X=approximately 10 degrees, but X could be other values as well. FIGS. 23-26 illustrate the relationship between the switch traveler 2170 and switches 2172, 2174, 2176 and the articulated position of the surgical end effector 1500. For example, in FIG. 25, when the switch traveler 2170 is in that position, the surgical end effector 1500 may be in a first articulated position on the first side of the shaft axis SA, wherein the surgical end effector axis EA is positioned at a first articulation angle $LA_1$ relative to the shaft axis SA. Likewise, when the switch traveler 2170 is in the position illustrated in FIG. 24, for example, the surgical end effector 1500 may be in a second articulated position located on a second side of the shaft axis SA, wherein the surgical end effector axis EA is positioned at a second articulation angle $LA_2$ relative to the shaft axis SA. In at least one arrangement, $LA_1=LA_2$=approximately 10°, for example.

Figures 27, 28:
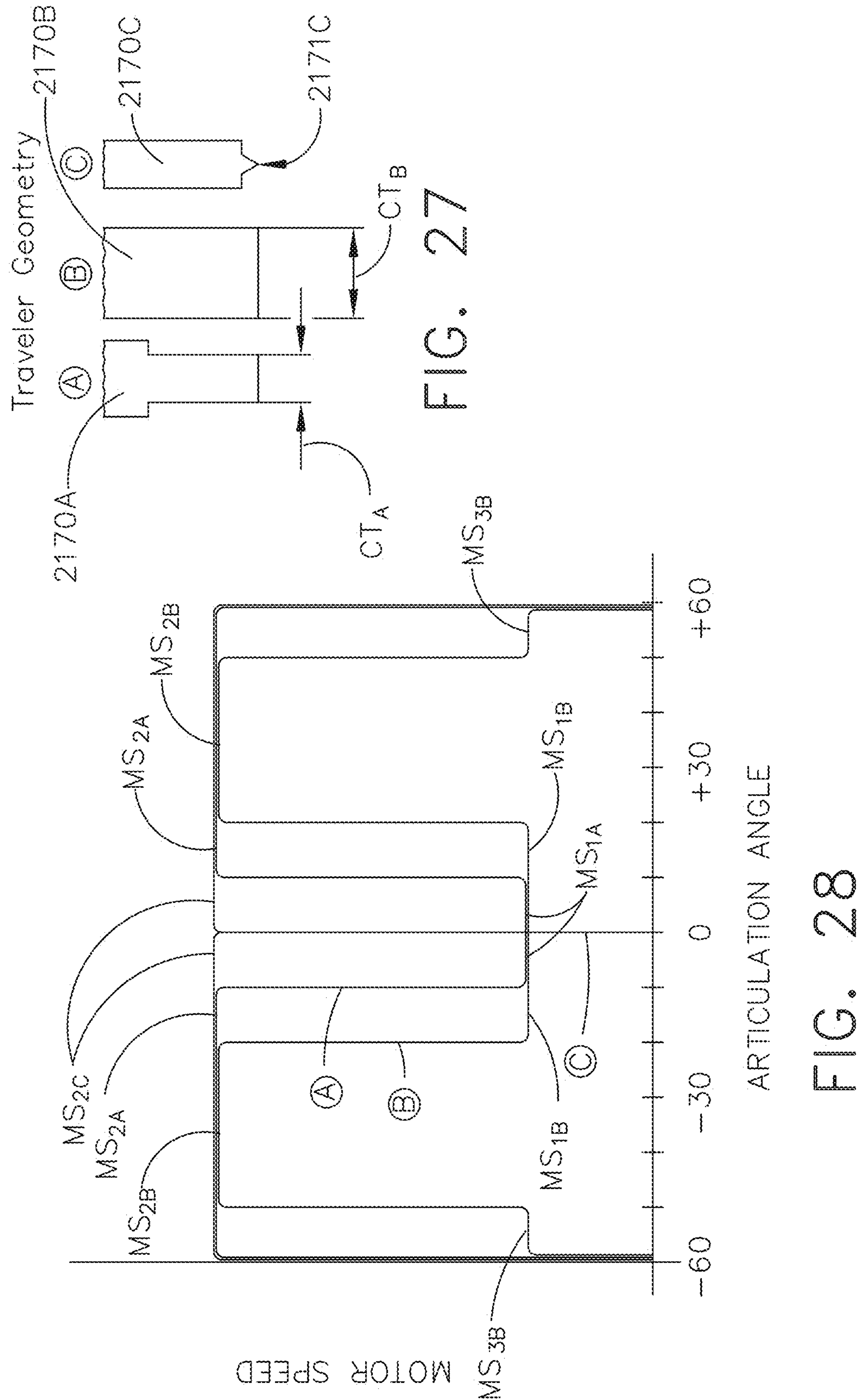
FIG. 27 depicts shapes of portions of three different switch traveler embodiments that may be employed in the switch system of FIG. 19.
FIG. 28 is a graphical comparison of motor speeds for each geometrical switch traveler shape depicted in FIG. 27 to an articulation angle of a surgical end effector coupled thereto.

FIG. 27 provides alternative geometrical shapes of the switch traveler 2170 when viewed from the free end of the switch traveler 2170 that is configured to interact with switches 2172, 2174, 2176. FIG. 28 is a graphical comparison of motor speeds (for each geometrical shape 2170A, 2170B, 2170C) to articulation angle. Switch traveler 2170A is also depicted in FIGS. 23-26. 2170C has an actuator point 21701C formed thereon for more precise actuation of the switches 2172, 2174, 2176. As can be seen in FIG. 28, the motor speed $MS_{2C}$ only drops off when the actuator point 2171C is in actuation contact with one of the switches 2172, 2174, 2176 which correspond to articulation angles of −60°, 0°, +60°. 2170A has a cross-sectional thickness $CT_A$ which results in a first motor speed $MS_{1A}$ for an articulation angle range between −10° to +10°. For articulation angles between −10° to −60° and +10° to +60°, the articulation motor 2140 may operate at a second motor speed $MS_{2A}$ that is greater than $MS_{1A}$. 2170B has a cross-sectional thickness $CT_B$ which is greater than the cross-sectional thickness $CT_A$ and results in a first motor speed $MS_{1B}$ for an articulation angle range between −20° to +20°. For articulation angles between −20° to −50° and +20° to +50°, the articulation motor 2140 may operate at a second motor speed $MS_{2B}$ that is greater than $MS_{1B}$. For articulation angles between −50 to −60 and +50 to +60 the articulation motor 2140 may operate at a third motor speed $MS_{3B}$. In the illustrated example, $MS_{3B}=MS_{1B}$.

Figure 28A:
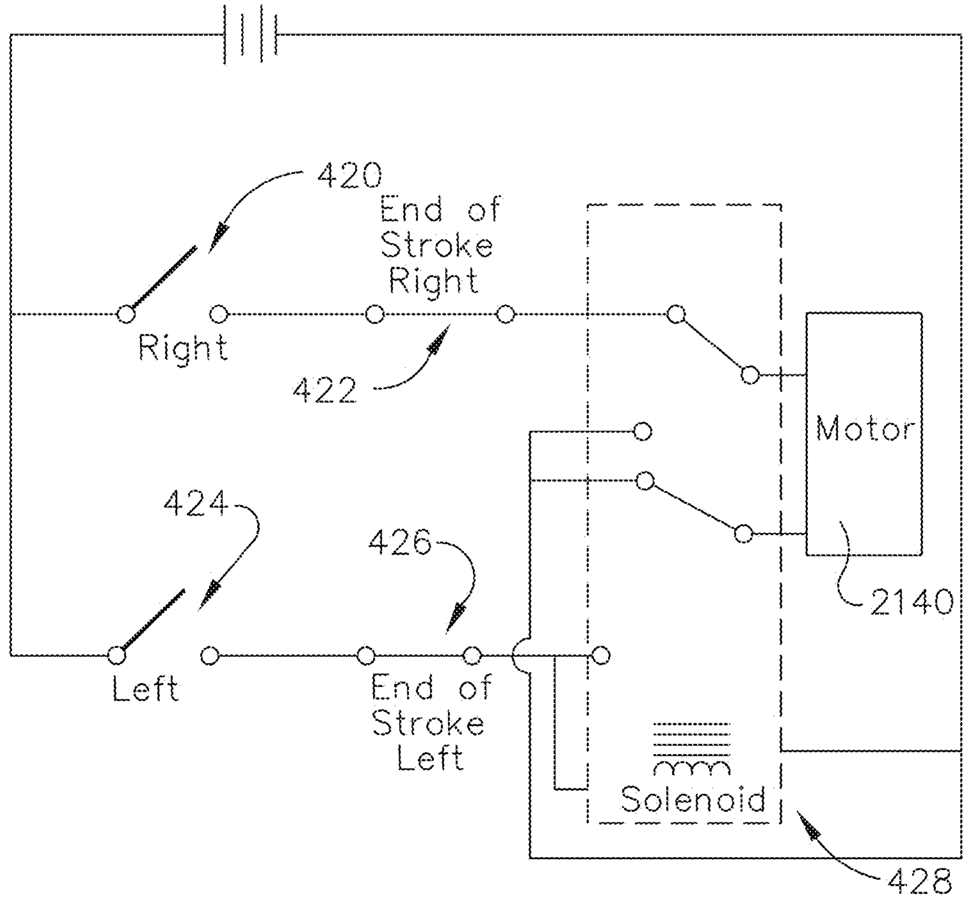
FIG. 28A illustrates one form of control circuit that may be employed to control an articulation motor of the powered surgical instrument of FIG. 16.

In various arrangements, the control circuit board 400 may include switches 420, 422, 424, 426 that define the articulation limits as well as a latchable or relay switch 428 that controls the center or home position of the end effector. See FIG. 28A. In such arrangement, as the articulation motor 2140 drives the end effector across the straight or home position, the latchable or relay switch 428 could be tripped which would deactivate the articulation motor 2140. Releasing the articulation control switch 2180 could activate a bypass relay which could deactivate the center or home switch 2172 and pressing the control switch 2180 again could allow the articulation to continue through the home position. See FIG. 28A.

EXAMPLES

Example 1—A surgical instrument comprising a first jaw and a second jaw that is operably supported relative to the first jaw such that the first and second jaws are movable between a closed position and an open position. The surgical instrument further comprises an axially movable closure member that is supported relative to the first and second jaws to apply closing and opening motions to at least one of the first and second jaws. A closure actuator operably interfaces with the axially movable closure member and is movable from an unactuated position corresponding to the open position in a closure direction during a closure procedure to cause the closure member to apply the closing motion to at least one of the first and second jaws. The surgical instrument further comprises a first means for applying an opening control motion to the closure actuator to return the closure actuator to the unactuated position upon completion of the closure procedure and a second means for applying a variable closure force to the closure member as the closure actuator is moved in the closure direction.

Example 2—The surgical instrument of Example 1, wherein the first means for applying comprises a first biasing member that interfaces with the closure actuator to return the closure actuator in an opening direction to the unactuated position after completion of the closure procedure.

Example 3—The surgical instrument of Example 2, wherein the second means for applying a variable closure force to the closure member comprises a second biasing member positioned between the closure member and the closure actuator to apply the variable closure force to the closure member as the closure actuator is moved in the closure direction.

Example 4—The surgical instrument of Example 3, wherein the first biasing member comprises a first compression spring and wherein the second biasing member comprises a second compression spring.

Example 5—The surgical instrument of Example 4, wherein the first compression spring comprises a first spring coefficient and wherein the second compression spring comprises a second spring coefficient that is greater than the first spring coefficient.

Example 6—The surgical instrument of Example 5, wherein the second spring coefficient is up to ten times greater than the first spring coefficient.

Example 7—The surgical instrument of Examples 1, 2, 3, 4, 5 or 6, wherein the first jaw comprises a surgical staple cartridge and wherein the second jaw comprises an anvil.

Example 8—The surgical instrument of Example 7, wherein the second jaw comprises an elongated channel that is configured to removably support the surgical staple cartridge therein.

Example 9—The surgical instrument of Examples 1, 2, 3, 4, 5, 6, 7 or 8, wherein the closure member comprises at least one actuator surface that is configured to cammingly contact at least one cam surface on one of the first and second jaws and at least one opening feature that is configured to engage a corresponding opening portion on one of the first and second jaws to apply opening motion thereto when the closure member is moved in an opening direction.

Example 10—The surgical instrument of Examples 1, 2, 3, 4, 5, 6, 7, 8 or 9, wherein the closure actuator comprises an axially movable shuttle member that operably interfaces with the closure member and a closure system that operably interfaces with the axially movable shuttle member to selectively move the axially movable shuttle member in the closing direction.

Example 11—The surgical instrument of Example 10, wherein the closure system comprises a closure trigger.

Example 12—A surgical instrument comprising a first jaw and a second jaw that os pivotally supported relative to the first jaw and is movable between an open position and a closed position relative to the first jaw upon application of opening and closing motions to the first jaw. An axially movable closure member is supported relative to the first and second jaws to apply the closing and opening motions to the second jaw. The surgical instrument further comprises a closure system that includes a closure actuator that operably interfaces with the axially movable closure member and is movable from an unactuated position corresponding to the open position of the second jaw in a first closure direction during a closure procedure to cause the closure member to apply the closure motion to the second jaw. The surgical instrument also includes a first means for applying an opening motion to the closure actuator to return the closure actuator to the unactuated position upon completion of the closure procedure and a second means for varying an amount of a closure force applied to the closure member by the closure actuator in relation to an amount of closure resistance experienced by the second jaw during the closure procedure.

Example 13—The surgical instrument of Example 12, wherein the first jaw comprises a surgical staple cartridge and wherein the second jaw comprises an anvil.

Example 14—The surgical instrument of Example 13, wherein the first jaw comprises an elongated channel that is configured to removably support the surgical staple cartridge therein.

Example 15—A surgical instrument comprising a surgical end effector that includes a first jaw and a second jaw that is operably supported relative to the first jaw such that the first and second jaws are movable between a closed position and an open position. The surgical instrument further comprises an elongated shaft assembly that is operably coupled to the surgical end effector. The elongate shaft assembly comprises an axially movable closure member that is configured to apply closing and opening motions to at least one of the first and second jaws. A housing is operably coupled to the elongated shaft assembly. The housing comprises a closure actuator operably interfaces with the axially movable closure member and is movable from an unactuated position corresponding to the open position in a closure direction during a closure procedure to cause the closure member to apply the closing motion to at least one of the first and second jaws. The surgical instrument further comprises a first means for applying an opening control motion to the closure actuator to return the closure actuator to the unactuated position upon completion of the closure procedure and a second means for applying a variable closure force to the closure member as the closure actuator is moved in the closure direction.

Example 16—The surgical instrument of Example 15, wherein the closure actuator comprises a shuttle member that is movably supported in the housing and operably interfaces with the closure member. A closure system is supported by the housing and operably interfaces with the shuttle member to selectively move the shuttle member in the closure direction.

Example 17—The surgical instrument of Example 16, wherein the closure system comprises a closure trigger that is movably supported by the housing.

Example 18—The surgical instrument of Examples 16 or 17, wherein the first means for applying comprises a first biasing member that is supported between a portion of the housing and the shuttle member to move the shuttle member in an opening direction after completion of the closure procedure and wherein the second means for applying a variable closure force to the closure member comprises a second biasing member supported between the closure member and the shuttle member.

Example 19—The surgical instrument of Example 18, wherein the first biasing member comprises a first compression spring and wherein the second biasing member comprises a second compression spring.

Example 20—The surgical instrument of Example 19, wherein the first compression spring comprises a first spring coefficient and wherein the second compression spring comprises a second spring coefficient that is greater than the first spring coefficient.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:

a housing;

a shaft extending from the housing, wherein the shaft defines a shaft axis;

an end effector rotatable relative to the shaft about an articulation axis;

a nozzle assembly to rotate the end effector about the shaft axis;

an articulation motor having a motor output gear which rotates about a motor axis, and actuatable to rotate the end effector about the articulation axis, wherein the articulation motor is mounted to the nozzle assembly, such that the motor axis is parallel to and offset from the shaft axis, and rotatable with the nozzle assembly;

an articulation drive to transmit an articulation motion from the articulation motor to the end effector to rotate the end effector about the articulation axis; and a gear assembly comprising gears to transmit a rotational drive motion output by the articulation motor to the articulation drive, wherein each of the gears of the gear assembly rotate about an axis parallel to and offset from an axis of rotation of another gear of the gear assembly and parallel to and offset from the shaft and motor axes.

2. The surgical instrument of claim 1, wherein the articulation drive comprises:

a proximal driver rotatable based on the actuation of the articulation motor; and a distal driver axially translatable along the shaft axis based on the rotation of the proximal driver.

3. The surgical instrument of claim 1, wherein the nozzle assembly comprises an internal surface defining a nozzle cavity, and wherein the articulation motor is positioned within the nozzle cavity.

4. The surgical instrument of claim 3, wherein the articulation motor outputs the rotational drive motion defined along the motor axis, wherein the motor axis is offset from the shaft axis, and wherein the motor axis orbits around the shaft axis based on rotation of the nozzle assembly.

5. The surgical instrument of claim 3, further comprising:

a control circuit;

an electrical contact fixed relative to the housing and positioned within the nozzle cavity; and a conductor mounted to the internal surface of the nozzle assembly, wherein the conductor remains in contact with it the electrical contact to electrically couple the articulation motor to the control circuit while the nozzle assembly rotates the end effector about the shaft axis.

6. The surgical instrument of claim 5, wherein the internal surface of the nozzle assembly defines an internal circumference of the nozzle assembly, and wherein the conductor is mounted to the internal surface of the nozzle assembly and extends along an entirety of the internal circumference of the nozzle assembly.

7. The surgical instrument of claim 6, further comprising a frame comprising a flange, wherein a first portion of the frame is positioned within the housing and a second portion of the frame comprising the flange extends into the nozzle cavity, wherein the nozzle assembly interfaces with and rotates about the flange, and wherein the electrical contact is mounted to the second portion of the frame.

8. The surgical instrument of claim 1, further comprising an articulation switch in signal communication with the articulation motor, wherein the articulation switch is movable to a first position to rotate the end effector in a first direction relative to the shaft, and wherein the articulation switch is movable to a second position to rotate the end effector in a second direction relative to the shaft.

9. The surgical instrument of claim 8, wherein the end effector defines an end effector axis, wherein a center position of the end effector corresponds to the end effector axis being aligned with the shaft axis, and wherein the actuation of the articulation motor is configured to stop based on the articulation switch being in the first position or the second position and the end effector rotating to the center position.

10. The surgical instrument of claim 9, wherein, the actuation of the articulation motor is configured to resume based on moving the articulation switch away from the first position or the second position and then returning the articulation switch to the first position or the second position.

11. The surgical instrument of claim 8, wherein the articulation switch is a rocker switch movable from a neutral position to the first position and from the neutral position to the second position.

12. The surgical instrument of claim 8, wherein the articulation switch comprises a first articulation switch, the surgical instrument further comprising a second articulation switch, wherein the first articulation switch and the second articulation switch are redundant switches positioned on opposite sides of the housing.

13. The surgical instrument of claim 1, further comprising:

a drive screw rotatable based on actuation of the articulation motor;

a switch traveler movable along a path defined by the drive screw based on rotation of the drive screw; and an articulation position switch positioned to interact with the switch traveler as the switch traveler moves along the path, wherein the articulation position switch is in signal communication with the articulation motor.

14. The surgical instrument of claim 13, wherein the articulation motor is configured to stop actuation or adjust a speed of actuation based on the switch traveler interacting the articulation position switch.

15. The surgical instrument of claim 14, wherein a position of the articulation position switch corresponds to an end of a range of rotation of the end effector.

16. The surgical instrument of claim 14, wherein a position of the articulation position switch corresponds to a center of a range of rotation of the end effector.

17. A surgical instrument comprising:

a handle assembly;

a shaft extending from the handle assembly, wherein the shaft defines a shaft axis;

an end effector pivotably coupled to a distal end of the shaft;

a nozzle assembly extending from the handle assembly and surrounding a proximal portion of the shaft, wherein the nozzle assembly is rotatable relative to handle assembly to roll the shaft and rotate the end effector about the shaft axis; and an articulation motor, within the nozzle assembly, having a motor output gear which rotates about a motor axis, and actuatable to pivot the end effector, wherein the articulation motor is mounted to the nozzle assembly such that the motor axis is parallel to and offset from the shaft axis;

an articulation drive to transmit an articulation motion from the articulation motor to the end effector to rotate the end effector about the articulation axis; and a gear assembly comprising gears to transmit a rotational drive motion output by the articulation motor to the articulation drive, wherein each of the gears of the gear assembly rotate about an axis parallel to and offset from an axis of rotation of another gear of the gear assembly and parallel to and offset from the shaft and motor axes.

18. A surgical instrument comprising:

a housing;

a shaft extending from the housing along a shaft axis;

an end effector rotatably coupled to a distal end of the shaft, the end effector comprising a first jaw and a second jaw movable relative to the second jaw;

a manual shaft roll actuator coupled to the shaft, wherein actuation of the manual shaft roll actuator causes the shaft to roll about the shaft axis; and a motor, having a motor output gear which rotates about a motor axis, to drive rotation of the end effector, wherein the motor is mounted to the manual shaft roll actuator such that the motor axis is parallel to and offset from the shaft axis;

an articulation drive to transmit an articulation motion from the motor to the end effector to rotate the end effector; and a gear assembly comprising gears to transmit a rotational drive motion output by the motor to the articulation drive, wherein each of the gears of the gear assembly rotate about an axis parallel to and offset from an axis of rotation of another gear of the gear assembly and parallel to and offset from the shaft and motor axes.

* * * * *